(12) United States Patent
Alexander et al.

(10) Patent No.: US 12,383,588 B2
(45) Date of Patent: *Aug. 12, 2025

(54) ZIKA VIRUS TREATMENT OF CD24-POSITIVE TUMORS AND DISEASES ASSOCIATED WITH ABNORMAL T CELL ACTIVATION AND TREATING OR PREVENTING ZIKA VIRUS INFECTIONS

(71) Applicant: THE NEMOURS FOUNDATION, Wilmington, DE (US)

(72) Inventors: Kenneth Andrew Alexander, Orlando, FL (US); Joseph Mazar, Orlando, FL (US); Tamarah Jeanette Westmoreland, Orlando, FL (US)

(73) Assignee: The Nemours Foundation, Wilmington, DE (US)

( * ) Notice: Subject to any disclaimer, the term of this patent is extended or adjusted under 35 U.S.C. 154(b) by 790 days.

This patent is subject to a terminal disclaimer.

(21) Appl. No.: 17/246,955

(22) Filed: May 3, 2021

(65) Prior Publication Data

US 2021/0322495 A1 Oct. 21, 2021

Related U.S. Application Data

(63) Continuation of application No. 16/056,086, filed on Aug. 6, 2018, now Pat. No. 10,993,975.

(60) Provisional application No. 62/542,094, filed on Aug. 7, 2017.

(51) Int. Cl.
| | | |
|---|---|---|
| *A61K 35/768* | (2015.01) | |
| *A61P 35/00* | (2006.01) | |
| *C07K 16/28* | (2006.01) | |

(52) U.S. Cl.
CPC ............ *A61K 35/768* (2013.01); *A61P 35/00* (2018.01); *C07K 16/2896* (2013.01); *C12N 2770/24132* (2013.01)

(58) Field of Classification Search
None
See application file for complete search history.

(56) References Cited

U.S. PATENT DOCUMENTS

| | | | |
|---|---|---|---|
| 10,786,537 | B2 | 9/2020 | Arumugaswami et al. |
| 10,993,975 | B2 * | 5/2021 | Alexander ............ A61K 35/768 |
| 2019/0038685 | A1 | 2/2019 | Alexander et al. |
| 2021/0145907 | A1 | 5/2021 | Diamond et al. |

OTHER PUBLICATIONS

Poncet C, et al. CD24, a glycosylphosphatidylinositol-anchored molecules is transiently expressed during the development of human central nervous system and is a marker of human neural cell lineage tumors. Acta Neuropathol. 1996;91(4):400-8. (Year: 1996).*

Carbaugh DL, Zhou S, Sanders W, Moorman NJ, Swanstrom R, Lazear HM. Two Genetic Differences between Closely Related Zika Virus Strains Determine Pathogenic Outcome in Mice. J Virol. Sep. 29, 2020;94(20):e00618-20. (Year: 2020).*

Su KY, Balasubramaniam VRMT. Zika Virus as Oncolytic Therapy for Brain Cancer: Myth or Reality? Front Microbiol. Nov. 20, 2019; 10:2715. (Year: 2019).*

Richner JM, Himansu S, Dowd KA, Butler SL, Salazar V, Fox JM, Julander JG, Tang WW, Shresta S, Pierson TC, Ciaramella G, Diamond MS. Modified mRNA Vaccines Protect against Zika Virus Infection. Cell. Mar. 9, 2017;168(6):1114-1125.e10. (Year: 2017).*

Ambros et al., "International consensus for neuroblastoma molecular diagnostics: report from the International Neuroblastoma Risk Group (INRG) Biology Committee," *British Journal of Cancer*, 2009, 100(9): 1471-1482.

Chiramel et al., "Role of Autophagy in Zika Virus Infection and Pathogenesis," *Virus Res.*, 2018, 254: 34-40. [Published online Sep. 9, 2017].

Dick et al., "Zika Virus (I). Isolations and serological specificity," *Transactions of the Royal Society of Tropical Medicine and Hygiene*, 1952, 46(5): 509-520.

Dundr and Ehrmann, "Neuronal Crest Cell-Derived Tumors: An Overview," Chapter 4 in Stem Cells and Cancer Stem Cells, Therapeutic Applications in Disease and Injury, 2012, 1:29-40, M. A Hayat, ed., Springer Science+Business Media B.V.

Fang et al., "CD24: From A to Z," *Cell. & Mol. Immun.*, 2010, 7: 100-113.

Hough et al., "Mapping of CD24 and homologous sequences to multiple chromosomal loci," *Genomics*, 1994, 22: 154-161.

Gilliam et al., "The CD24 surface antigen in neural development and disease," *Neurobiology of Disease*, 2017, 99: 133-144. [Published online Dec. 18, 2016].

Ma and Chung, "Quantitative Analysis of Copy No. Unit 7.21 Variants Based on Real-Time LightCycler PCR," *Curr. Protoc. Hum. Genet.*, 2014, 80: 7.21.1-7.21.8.

Reynolds et al., "Retinoid therapy of high-risk neuroblastoma," *Cancer Lett.*, 2003, 197(1-2): 185-192.

"SYBR Green I Dye Detection Protocol" in a Technical Guide to PCR Technologies, Sigma-Aldrich Co. LLC (2017), https://www.sigmaaldrich.com/technical-documents/protocols/biology/sybr-green-i-dye-quantitative-pcr.html.

Wang et al., "A Dinucleotide Deletion in CD24 Confers Protection against Autoimmune Diseases," *PLoS Genet.*, 2007, 3(4): e49. https://doi.org/10.1371/journal.pgen.0030049.

(Continued)

*Primary Examiner* — Benjamin P Blumel

(74) *Attorney, Agent, or Firm* — Faegre Drinker Biddle & Reath LLP

(57) ABSTRACT

CD24-positive malignant and benign tumors are treated by administration of a naturally occurring or modified oncolytic Zika virus. Diseases associated with abnormal T cell activation or T cell-mediated autoimmunity, wherein CD24 expression is increased, are also expected to be treated by administration of a naturally occurring or modified oncolytic Zika virus. Also contemplated are compounds and methods for treating and/or preventing Zika virus infection in a subject.

16 Claims, 17 Drawing Sheets
(4 of 17 Drawing Sheet(s) Filed in Color)
Specification includes a Sequence Listing.

(56) References Cited

OTHER PUBLICATIONS

Zhu et al., "Brain Metastasis in Children with Stage 4 Neuroblastoma after Multidisciplinary Treatment," *Chinese Journal of Cancer*, 2015, 34:49.
Mazar et al., "Zika virus as an oncolytic treatment of human neuroblastoma cells requires CD24," *PLoS One*, 2018, 13(7): e0200358. https://doi.org/10.1371/journal.pone.0200358 [related new publication].

* cited by examiner

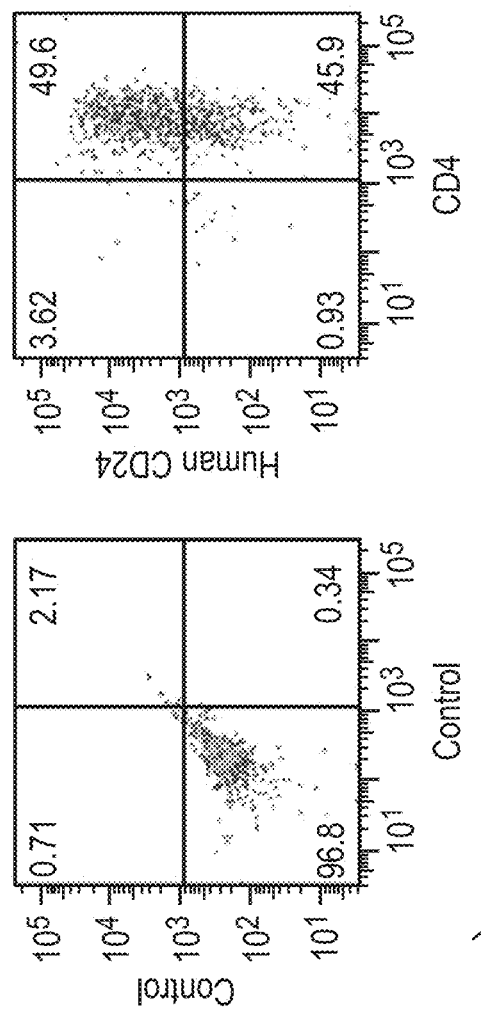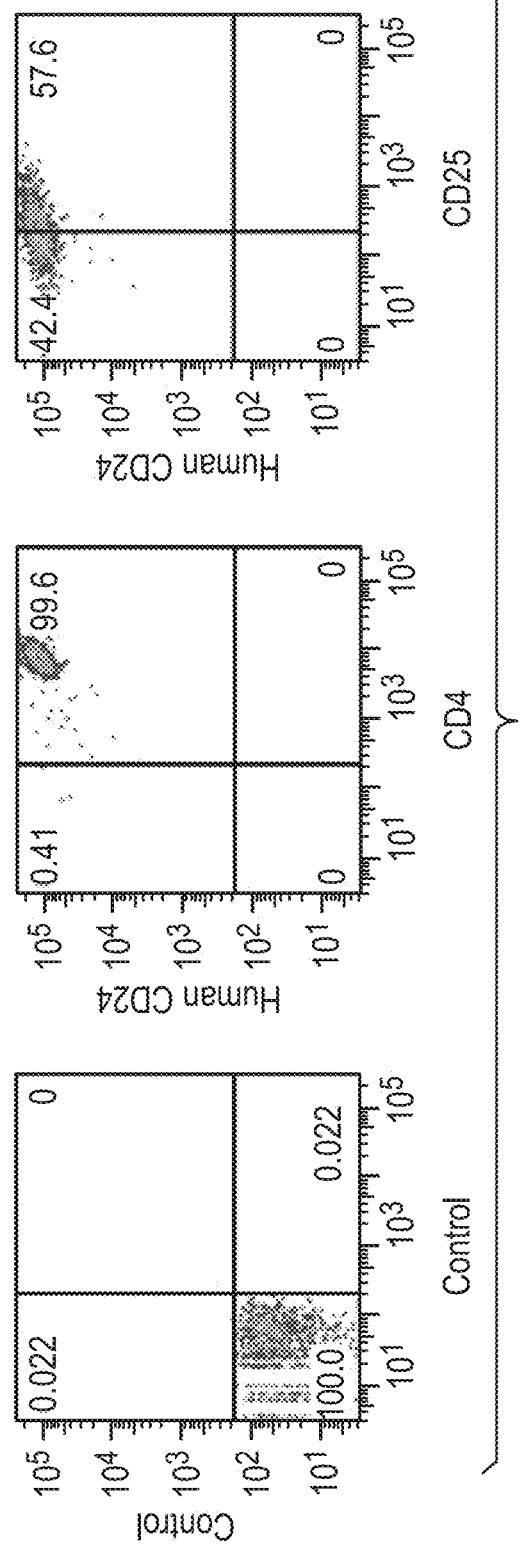

SEQUENCE LISTING

<160> NUMBER OF SEQ ID NOS: 9

<210> SEQ ID NO 1
<211> LENGTH: 19
<212> TYPE: DNA
<213> ORGANISM: Artificial Sequence
<220> FEATURE:
<223> OTHER INFORMATION: Synthetic oligomer
<220> FEATURE:
<221> NAME/KEY: misc_feature
<222> LOCATION: (1)..(19)
<223> OTHER INFORMATION: GAPDH, sense primer

<400> SEQUENCE: 1
acatcgctca gacaccatg                                                    19

<210> SEQ ID NO 2
<211> LENGTH: 22
<212> TYPE: DNA
<213> ORGANISM: Artificial Sequence
<220> FEATURE:
<223> OTHER INFORMATION: Synthetic oligomer
<220> FEATURE:
<221> NAME/KEY: misc_feature
<222> LOCATION: (1)..(22)
<223> OTHER INFORMATION: GAPDH, anti-sense primer

<400> SEQUENCE: 2
tgtagttgag gtcaatgaag gg                                                22

<210> SEQ ID NO 3
<211> LENGTH: 22
<212> TYPE: DNA
<213> ORGANISM: Artificial Sequence
<220> FEATURE:
<223> OTHER INFORMATION: Synthetic oligomer
<220> FEATURE:
<221> NAME/KEY: misc_feature
<222> LOCATION: (1)..(22)
<223> OTHER INFORMATION: CD24 variant 001, sense primer

<400> SEQUENCE: 3
ctgctgctgc tggcactgct cc                                                22

<210> SEQ ID NO 4
<211> LENGTH: 22
<212> TYPE: DNA
<213> ORGANISM: Artificial Sequence
<220> FEATURE:
<223> OTHER INFORMATION: Synthetic oligomer
<220> FEATURE:
<221> NAME/KEY: misc_feature
<222> LOCATION: (1)..(22)
<223> OTHER INFORMATION: CD24 variant 001, anti-sense primer

<400> SEQUENCE: 4
ggggccaacc cagagttgga ag                                                22

<210> SEQ ID NO 5
<211> LENGTH: 22
<212> TYPE: DNA
<213> ORGANISM: Artificial Sequence
<220> FEATURE:
<223> OTHER INFORMATION: Synthetic oligomer
<220> FEATURE:
<221> NAME/KEY: misc_feature
<222> LOCATION: (1)..(22)
<223> OTHER INFORMATION: CD24 variant 007, sense primer

<400> SEQUENCE: 5

```
ctgggcctgg gagaccctag cg                                               22

<210> SEQ ID NO 6
<211> LENGTH: 22
<212> TYPE: DNA
<213> ORGANISM: Artificial Sequence
<220> FEATURE:
<223> OTHER INFORMATION: Synthetic oligomer
<220> FEATURE:
<221> NAME/KEY: misc_feature
<222> LOCATION: (1)..(22)
<223> OTHER INFORMATION: CD24 variant 007, anti-sense primer

<400> SEQUENCE: 6
ggggccaacc cagagttgga ag                                               22

<210> SEQ ID NO 7
<211> LENGTH: 28
<212> TYPE: DNA
<213> ORGANISM: Artificial Sequence
<220> FEATURE:
<223> OTHER INFORMATION: Synthetic oligomer
<220> FEATURE:
<221> NAME/KEY: misc_feature
<222> LOCATION: (1)..(28)
<223> OTHER INFORMATION: CD24 - 001 ORF For (BamHI) primer

<400> SEQUENCE: 7
tggatccatg ggcagagcaa tggtggcc                                         28

<210> SEQ ID NO 8
<211> LENGTH: 28
<212> TYPE: DNA
<213> ORGANISM: Artificial Sequence
<220> FEATURE:
<223> OTHER INFORMATION: Synthetic oligomer
<220> FEATURE:
<221> NAME/KEY: misc_feature
<222> LOCATION: (1)..(28)
<223> OTHER INFORMATION: CD24 - 007 ORF For (BamHI) primer

<400> SEQUENCE: 8
tggatccatg gtgggacgat tctgtccc                                         28

<210> SEQ ID NO 9
<211> LENGTH: 36
<212> TYPE: DNA
<213> ORGANISM: Artificial Sequence
<220> FEATURE:
<223> OTHER INFORMATION: Synthetic oligomer
<220> FEATURE:
<221> NAME/KEY: misc_feature
<222> LOCATION: (1)..(36)
<223> OTHER INFORMATION: CD24 ORF Rev (EcoRI) primer

<400> SEQUENCE: 9
agaattctta agagtagaga tgcagaagag agagtg                                36
```

ZIKA VIRUS TREATMENT OF CD24-POSITIVE TUMORS AND DISEASES ASSOCIATED WITH ABNORMAL T CELL ACTIVATION AND TREATING OR PREVENTING ZIKA VIRUS INFECTIONS

CROSS-REFERENCE TO RELATED APPLICATION APPLICATIONS

This application is a continuation of co-pending U.S. patent application Ser. No. 16/056,086 filed on Aug. 6, 2018, now allowed, which claims priority to U.S. Provisional Application No. 62/542,094 filed on Aug. 7, 2017, the disclosures of which are hereby incorporated by reference in their entirety.

REFERENCE TO A SEQUENCE LISTING

The instant application contains a sequence listing which has been submitted in ASCII format via EFS-Web and is hereby incorporated by reference in its entirety. Said ASCII copy, created on Apr. 30, 2021, is named 045009_0051_01_000004_SL.txt and is 2,924 bytes in size.

FIELD

The invention relates to the field of treatment of cancer, and to diseases associated with abnormal T cell activation or T cell-mediated autoimmunity, the use of an oncolytic Zika virus for treatment of cancer and to diseases associated with abnormal T cell activation or T cell-mediated autoimmunity, and to developing novel compounds for treating or preventing Zika virus infection.

BACKGROUND

Children and adults develop tumors that arise from the embryonic neural crest. The latter is a transient structure in vertebrate embryos that gives rise to a population of pluripotent cells that contribute to the formation of multiple tissues and organs throughout the body. Malignant cells mimic many of the behavioral, molecular, and morphologic aspects of neural crest development. This carefully regimented program that normally balances proliferation with differentiation, migration with inhibition, and pluripotency with specification during development can be co-opted by the malignant cell for growth, invasion, and metastasis. Mutations in mature cells may be responsible for reactivating their embryonic developmental programs and initiating tumorigenesis and metastasis. Alternatively, a population of primitive and undifferentiated neural crest stem cells may persist in crest-derived tissues awaiting the proper environmental or cellular cues to stimulate them. Tumorigenesis may thus result in cells derived from the neural crest. Such tumors are referred to herein variously as "neural crest-derived tumors".

One group of neural crest-derived tumors are tumors of sympatho-adrenal lineage. They include neuroblastoma, paraganglioma, and pheochromocytoma.

Paraganglioma and pheochromocytomas are highly vascularized tumors arising from neural crest-derived tissues in the paraxial autonomic ganglia or in the chromaffin cells of the adrenal medulla, respectively. Paraganglioma and pheochromocytomas may manifest as head and neck cancers.

Neuroblastoma is the most common tumor of infancy, accounting for 7-10% of all childhood cancers. Neuroblastoma accounts for 6% of tumors in children ages 0-14 years. Approximately 700 cases of neuroblastoma occur each year in the United States, most in the first year of life, and almost all occurring in children under age 5 years.

Primary neuroblastoma occurs within the adrenal medulla and paraspinal sympathetic ganglia, with metastases to other tissues occurring in half of patients. Prognosis varies widely, with a particularly poor prognosis in aggressive disease.

Neuroblastomas are characterized according to risk level. Thirty-seven percent of neuroblastoma cases are low risk, 18% are intermediate risk, and 45% are high risk. Low risk patients may be successfully treated with surgery alone (or no treatment), while intermediate risk patients are treated with a combination of surgery and chemotherapy. High risk patients are treated with a multi-modal therapy that may consist of chemotherapy, surgery, radiation therapy, 13-cis-retinoic acid therapy, stem cell transplantation and/or antibody immunotherapy. Between 20% and 50% of high-risk neuroblastoma patients do not respond to therapy. Relapse is common. Long-term survival for children with advanced disease older than 18 months of age is poor.

Another group of neural crest-derived tumors are tumors of melanocytes, i.e., melanomas. Melanoma is generally curable, if recognized and treated early. Depending on the stage, melanoma may be treated by surgery and/or radiation, with excision of surrounding lymph nodes, and adjuvant chemotherapy. However, melanoma has a high metastatic potential. If not treated early, melanoma can advance and spread to other parts of the body, where treatment becomes difficult, resulting in fatality. If diagnosed before metastasis occurs, surgical excision can often provide an effective, long-term treatment. However, following cellular metastasis, the lesion becomes malignant, and most current therapies including chemotherapy offer little, to no therapeutic benefit.

While melanoma is not the most common of the skin cancers, it causes the most deaths. Malignant melanoma causes 48,000 deaths worldwide annually. Recently, life span has been extended in advanced (stage IV) melanoma patients with "checkpoint inhibitor" immunotherapy drugs such as pembrolizumab (Keytruda®), nivolumab (Opdivo®), and ipilimumab (Yervoy®). There is a need for an effective, specific treatment in view of the increasing incidence of melanoma worldwide.

Another group of neural crest-derived tumors are tumors of Schwann cell lineage. Schwann cell precursors give rise to a variety of cell types, including melanocytes, neurons, fibroblasts, Schwann cells, and parasympathetic ganglia. Schwann cells can give rise to a variety of tumors, including neurofibromas (type 1, also known as von Recklinghausen's disease; and type 2), malignant peripheral nerve sheath tumors, and schwannomas. Type 1 neurofibromas are Schwann cell-derived tumors containing fibroblasts, mast cells, and dendritic cells, in addition to Schwann cells. Type 2 neurofibromatosis is associated with schwannomas, which are encapsulated, uniform tumors of mature Schwann cells with minimal malignant potential.

Yet another group of neural crest-derived tumors are type A/B multiple endocrine neoplasias, characterized by multiple tumors of neural crest-derived tissues.

Surgery is typically used as the primary treatment for early stages of cancer. However, many tumors cannot be completely removed by surgical means. The efficacy of chemotherapy is often limited by severe side effects, including nausea and vomiting, bone marrow depression, renal damage, and central nervous system depression. Radiation therapy relies on the greater ability of normal cells, in contrast with neoplastic cells, to repair themselves after treatment with radiation. Radiotherapy cannot be used to treat many neoplasms, however, because of the sensitivity of tissue surrounding the tumor.

Current treatments for neural crest-derived tumors generally rely on these methods of surgery, chemotherapy, radiation therapy and, more recently, antibody immunotherapy. Some of these treatments have led to improvements in cancer survival, but often at the cost of significant associated morbidity. Despite these efforts, neuroblastoma and melanoma, in particular, are characterized by a high rate of mortality, especially in advanced stages. The survival rate for stage IV neuroblastoma is only 20%. The survival rate for stage IV melanoma is also ~20%. Cancer therapeutics for advanced stage neuroblastoma and melanoma are often ineffective.

While neuroblastoma in early infancy often resolve spontaneously and may not need medical treatment, neuroblastoma in older children often requires surgical treatment followed by chemotherapy and radiation therapy. Children with neuroblastoma refractory to therapy may undergo intensive chemotherapy with autologous bone marrow transplantation. Given these treatments, the care of patients with neuroblastoma is very expensive. Because there is a significant rate of therapeutic failure resulting in the deaths of children, the need for further effective novels therapies is high.

What is needed is an alternative, effective treatment for neural crest-derived tumors, neuroblastomas and melanomas in particular, that address the shortcomings of the existing treatments.

SUMMARY

Provided is an oncolytic Zika virus for treating (1) a CD24 positive tumor in an individual wherein, the tumor comprising malignant cells characterized by the presence of CD24, or (2) a disease associated with abnormal T cell activation or a T cell-mediated autoimmunity, wherein abnormal T cell activation or T cell-mediated autoimmunity results in increased CD24 expression.

Also provided is a pharmaceutical composition comprising a pharmaceutically acceptable carrier and an oncolytic Zika virus, for use in treating (1) a tumor expressing CD24 comprising malignant cells characterized by the presence of CD24, or (2) a disease associated with abnormal T cell activation or a T cell-mediated autoimmunity, wherein abnormal T cell activation or T cell-mediated autoimmunity results in increased CD24 expression.

Additionally provided is the use of an oncolytic Zika virus, for preparation of a medicament for treating (1) a tumor expressing CD24 comprising malignant cells characterized by the expression of CD24 on the tumor cells, or (2) a disease associated with abnormal T cell activation or a T cell-mediated autoimmunity, wherein abnormal T cell activation or T cell-mediated autoimmunity results in increased CD24 expression.

Described herein is a method for treating a CD24 positive tumor in an individual in need of such treatment, the tumor comprising malignant cells characterized by the presence of CD24, the method comprising administering to the subject an effective amount of an oncolytic Zika virus. The method can further be for the treatment of a CD24 positive tumor, wherein the tumor is selected from the group consisting of: an ovarian cancer, a colorectal cancer, a B cell lymphoma, erythroleukemia, a glioma, a small cell lung cancer, an esophageal squamous cell carcinoma, a hepatocellular carcinoma, a hepatoblastoma, a cholangiocarcinoma, a pancreatic adenocarcinoma, a melanoma, an urothelial carcinoma, a breast cancer, a primary neuroendocrine carcinoma, a neural crest-derived tumor, an HPV-associated malignancy, an Epstein-Barr virus-induced malignancy, and a prostate carcinoma. The HPV-associated malignancy may be selected from the group consisting of cervical cancer or precancer, vaginal, vulvar, and anal precancers or cancers, and oropharyngeal precancers or cancers. The Epstein-Barr virus-induced malignancy may be selected from the group consisting of nasopharyngeal carcinoma, lymphoma, and post transplantation lymphoma proliferative disease.

The method can be for when the tumor is a neural crest-derived tumor and is located in the brain. Such neural crest-derived tumors can be selected from the group consisting of: a neuroblastoma, a glioma, and a melanoma. The method can be used for when the tumor is a melanoma. The tumor contemplated for use with the method may be a refractory tumor.

The Zika virus use for the method can be naturally occurring or a modified Zika virus. The Zika virus can be any of the oncolytic Zika virus strains discussed herein, but preferably is not the same strain as used in a Zika vaccine received by the subject to be treated.

The method can utilize an oncolytic Zika virus wherein the Zika virus is in the form of virus particles. The method can also be wherein the virus is in the form of naked viral RNA. The naked viral RNA can be also administered in a liposome composition wherein the naked viral RNA is contained in the liposome.

The method can be one that when the subject in need thereof is treated with the effective amount, at least about 10% of the CD24-expressing tumor cells are lysed. The method can be also wherein at least about 50% of the cells of the CD24 expressing tumor cells are lysed.

The method can administer the oncolytic Zika virus intralesionally to the neural crest-derived tumor or CD24-positive tumor. The oncolytic Zika virus can also be administered via injection in the method. Alternatively, the oncolytic Zika virus can be administered topically, intradermally, or systemically in the methods described herein. For systemic administration, the oncolytic Zika virus can be administered by intravenous injection or infusion.

The method can further comprise administering to the subject an immunosuppressive therapy to facilitate or enhance lysis of the oncolytic Zika virus treatment. The immunosuppressive therapy can include an immunosuppressive pharmaceutical agent, administration of anti-antivirus antibody directed against antibodies that recognize the administered oncolytic Zika virus, plasmapheresis of the subject to remove antibodies that recognize the administered oncolytic Zika virus, administration of non-specific immunoglobulin, administration of anti-CD4 and/or anti-CD8 antibodies, or complement neutralization.

The methods described herein can further be combined with another anti-neoplasm treatment selected from chemotherapy, radiotherapy, surgery, hormone therapy and/or immunotherapy.

Another aspect described herein is a monoclonal antibody or a fragment thereof that binds to a Zika virus and blocks binding by the Zika virus to CD24 on a CD24-expressing cell.

A further aspect described herein is a monoclonal antibody or a fragment thereof that binds to CD24 and blocks binding by a Zika virus to CD24 on a CD24 expressing cell.

The described monoclonal antibodies or fragments thereof that bind to either a Zika virus or to CD24 and through the binding block Zika virus infection in a cell or in a subject can be used in a method to treat or prevent Zika virus infection in a subject by administering the monoclonal antibody or fragment thereof to the subject in an effective amount. The subject can be a human, a human in a Zika virus prone geographical area, a subject believed to have been exposed to a Zika virus or a health care worker with a high likelihood of exposure to a patient with Zika virus. The human can be a pregnant human.

Also contemplated is a method of preventing a Zika virus infection in a subject by administering an attenuated Zika virus, to induce antibodies that bind to the Zika virus and block binding by the Zika virus to CD24 on a CD24-expressing cell.

Also described is a method of preventing a Zika virus infection in a subject by administering a Zika virus CD24 binding protein, to induce antibodies that bind to the Zika virus and block binding by the Zika virus to CD24 on a CD24-expressing cell.

Further described herein is a method for treating a diseases associated with abnormal T cell activation or a T cell-mediated autoimmunity in an individual in need of such treatment, wherein abnormal T cell activation or T cell-mediated autoimmunity results in increased CD24 expression in the individual, the method comprising administering to the individual an effective amount of an oncolytic Zika virus.

The method can utilize an oncolytic Zika virus wherein the Zika virus is in the form of virus particles. The method can also be wherein the virus is in the form of naked viral RNA. The naked viral RNA can be also administered in a liposome composition wherein the naked viral RNA is contained in the liposome.

The diseases associated with abnormal T cell activation or T cell-mediated autoimmunity may be a rheumatologic disorder selected from the group consisting of rheumatoid arthritis, juvenile idiopathic arthritis, lupus nephritis, lupus vasculitis, pyomyositis, dermatomyositis, scleroderma, Sjogren's disease, ankylosing spondylitis, temporal arteritis, autoimmune vasculitis, sarcoidosis, Kawasaki disease, psoriatic arthritis, system sclerosis, Behçet's disease, and mixed connective tissue disorder. The diseases associated with abnormal T cell activation or T cell-mediated autoimmunity may be a neurological disease selected from the group consisting of multiple sclerosis, chronic inflammatory demyelinating polyneuropathy, and Guillain-Barré syndrome. The diseases associated with abnormal T cell activation or T cell-mediated autoimmunity may be a gastroenterological disease selected from the group consisting of ulcerative colitis, Crohn's disease, primary biliary cirrhosis, autoimmune pancreatitis, and autoimmune hepatitis. The diseases associated with abnormal T cell activation or T cell-mediated autoimmunity may be a dermatological disease selected from the group consisting of alopecia areata, psoriasis, vitiligo, and eczema. The diseases associated with abnormal T cell activation or T cell-mediated autoimmunity may be an endocrine disease selected from the group consisting of Hashimoto thyroiditis, type 1 diabetes mellitus, Graves' disease, and autoimmune polyendocrine syndrome. The diseases associated with abnormal T cell activation or T cell-mediated autoimmunity may be a hematological disease selected from the group consisting of autoimmune myelodysplastic syndromes, aplastic anemia, graft-versus-host disease, and hemophogocytic syndromes. The diseases associated with abnormal T cell activation or T cell-mediated autoimmunity may be an infectious disease selected from the group consisting of HIV infection, post-transplantation lymphoproliferative disorder due to Epstein-Barr virus, and myocarditis. The diseases associated with abnormal T cell activation or T cell-mediated autoimmunity may be a T-cell-mediated acute graft rejection.

As envisioned in the present invention with respect to the disclosed compositions of matter and methods, in one aspect the embodiments of the invention comprise the components and/or steps disclosed herein. In another aspect, the embodiments of the invention consist essentially of the components and/or steps disclosed herein. In yet another aspect, the embodiments of the invention consist of the components and/or steps disclosed herein.

Furthermore, it is to be understood that the description that follows encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group.

DESCRIPTION OF THE FIGURES

The patent or application file contains at least one drawing executed in color. Copies of this patent or patent application publication with color drawing(s) will be provided by the Office upon request and payment of the necessary fee.

FIG. 4A shows the immunofluorescence labeling of Zika viral Envelope protein in IMR-32 and SK-N-AS cells at Day 3 post-infection. Envelope staining is in red (Alexa Fluor 647) and nuclei are stained in blue (DAPI). Samples are also shown together (merged). Cells were scanned using a Nikon™ AIR VAAS laser point- and resonant-scanning confocal microscope. Images are at a magnification of 40× with a 4× zoom. FIG. 4B shows 3-dimensional Z-stacks of the immunofluorescent labeling of Zika viral Envelope protein in IMR-32 and SK-N-AS cells at Day 3 post-infection. The images presented are merged. Z-stacking was performed using NIS-Elements 4.5 imaging software.

FIG. 5A shows the schematic of the alignment of CD24 splice variants 1 and 7. FIGS. 5B and 5C show absolute quantification of CD24 expression by quantitative real-time PCR of total RNA acquired from neuroblastoma cells, measuring CD24 splice variants 1 (FIG. 5B) and 7 (FIG. 5C). Copy number values were normalized to the corresponding GAPDH values to determine the relative copy number. ** p<0.05, Student's t-test. FIG. 5D shows Western blot analysis of CD24 expression in the total cell lysates of neuroblastoma cells compared to Vero cell control. GAPDH was used as a loading control. All results are representative of the combined data of experiments performed in triplicate, with error bars representing standard deviation. FIG. 5E shows Western blot analysis of Zika virus infections in SK-N-As cells (a human neuroblastoma cell line, ATCC CRL-2137) after transient transfection of recombinant CD24 splice variants (compared to Vero cell control). Analysis performed for Zika envelope protein and NS1 (Non-Structural 1) protein compared to GAPDH control.

FIG. 6A shows a Western blot of CD24 knock-down in IMR32 cells as compared to a negative control (Neg Con) siRNA prior to Zika infection. FIG. 6B shows a Western blot of NS1 and envelope proteins in IMR32 cells (human small neuroblast-like cells) after CD24 knock-down (KD) and Zika infection as compared to the negative control siRNA and uninfected cells.

FIG. 9A shows SK-N-AS wild-type cells that are either infected (In) or uninfected (Un) by a Zika virus. FIG. 9B shows SK-N-AS cells that express vector only that are either infected or uninfected by Zika virus. FIG. 9C shows SK-N-AS/CD24 v1, and FIG. 9D depicts SK-N-AS-/CD24 v7.

FIG. 10C shows the results of viral titer (TCID50) assays of SK-N-AS/VO, SK-N-AS/CD24 v1, and SK-N-AS/CD24 v7 cells at Day 2 and 3 post-infection. Data is composed of three biological replicates examined in sextuplicate, with error bars representing standard deviation.  p<0.05, Student's t-test. FIG. 10D shows the immunofluorescence labeling of Zika viral Envelope protein in SK-N-AS/VO, SK-N-AS/CD24 v1, and SK-N-AS/CD24 v7 cells at Day 3 post-infection. Envelope staining is in red (Alexa Fluor 647) and nuclei are stained in blue (DAPI). Samples are also shown together (merged). Cells were scanned using a Nikon™ AIR VAAS laser point- and resonant-scanning confocal microscope. Images are at a magnification of 40× with a 4× zoom. FIG. 10E shows 3-Dimensional Z-stacks of the immunofluorescent labeling of Zika viral Envelope protein in CD24-expressing SK-N-AS cells. The images presented are merged. Z-stacking was performed using NIS-Elements 4.5 imaging software. All results are representative of the combined data of experiments performed in triplicate.

FIG. 13A shows CD24 variant 1 mRNA expression levels in IMR32 neuroblastoma cells, SK-N-AS neuroblastoma cells, and HUH-6 hepatoblastoma cells. FIG. 13B shows Zika virus-induced lysis of HUH-6 cells. HUH-6 cells were mock-treated or treated with MOI=10 Zika virus. After 4 days, cells were photographed using phase contrast bright field microscopy (10× magnification). The uninfected cells grew to confluence. The Zika virus-treated HUH-6 hepatoblastoma cells dies. Residual cells are rounded and isolated, as is characteristic of apoptotic cells.

FIGS. 15A, 15B, and 15C depict the observation that CD24 is expressed on primary activated CD4 T-cells. Human CD4+ T-cells were purified and stimulated for three days with anti-CD3 and anti-CD28 antibodies. The anti-CD3/28 stimulating antibodies were then removed and the primary activated CD4+ T-cells were continued to be cultured in complete RPMI 1640 media plus interleukin-2. On days 3 and 10 following T-cell activation with the CD3/CD28 antibodies, expression of the cellular surface markers CD4, CD 24, and CD 25 were assessed by flow cytometry using anti-CD4, anti-CD24 and anti-CD25 antibodies. As shown in FIGS. 15A and 15B, CD4-positive T cells express increasing amounts of CD24 following CD3/CD28 activation. FIG. 15C is a positive control experiment conforming that the CD24 antibody detects CD24 on IMR-32 neuroblastoma cells.

DEFINITIONS

Figure 1:
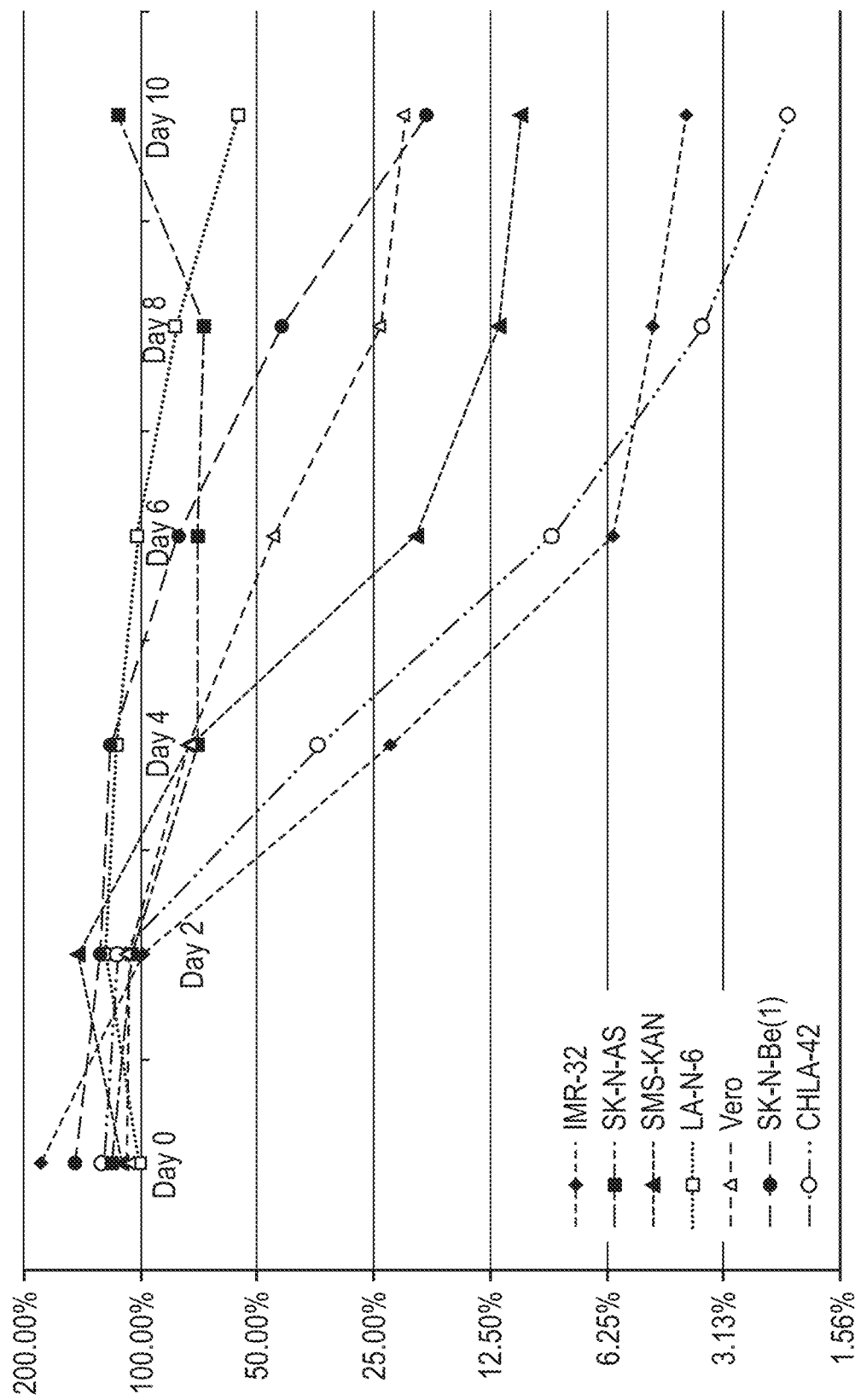
FIG. 1 depicts cell viability of human neuroblastoma cells infected by Zika virus over a 10 day period (compared to a Vero cell control). All infections were performed at MOI=10 and the results shown are compared to uninfected control cells for each cell line.

Unless defined otherwise, all technical and scientific terms used herein have the same meaning as commonly understood by one of ordinary skill in the art to which the invention pertains.

Although any methods and materials similar or equivalent to those described herein can be used in the practice for testing of the present invention, the preferred materials and methods are described herein. In describing and claiming the present invention, the following terminology will be used. It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

As used herein, the term "and/or" includes any and all combinations of one or more of the associated listed items.

"About" as used herein when referring to a measurable value such as an amount, a temporal duration, and the like, indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters. As used herein, the term "about" means that the number being described can deviate by plus or minus five percent of the number. For example, "about 250 g" means from 237.5-262.5 g. When the term "about" is used in a range, then the lower limit may be as much as minus 5% of the lower number and the upper limit may extend up to plus 5% of the upper number. For example, a range of about 100 to about 200 g indicates a range that extends from as low as 95 g up to 210 g.

An "effective amount" as used herein, means an amount which provides the intended effect. For an oncolytic virus used to treat or ameliorate a tumor, an effective amount is an amount of the virus sufficient to alleviate or eliminate the symptoms of the tumor or to slow down the progression of the tumor in a subject. It is understood, however, that the full therapeutic effect does not necessarily occur by administration of one dose, and may occur only after administration of a series of doses. Thus, an effective amount may be administered in one or more administrations. In the context of therapeutic or prophylactic applications, the amount of active agent administered to the subject will depend on the type and severity of the disease or condition and on the characteristics of the subject, such as general health, age, sex, body weight and tolerance to drugs. It will also depend on the degree, severity and type of disease or condition. The skilled artisan will be able to determine appropriate dosages depending on these and other factors.

As used herein, "individual" or "patient" or "subject" (as in the subject of the treatment) means both mammals and non-mammals. Mammals include, for example, humans; non-human primates, e.g. apes and monkeys; cattle; horses; sheep; and goats. Non-mammals include, for example, fish and birds.

As used herein, "level of amplification" with reference to a particular gene means the gene's copy number in the genome of a cell. A copy number of about 10-fold or more above the copy number of a gene in normal cells of a corresponding normal tissue means that the gene is "amplified".

As used herein, the term "pharmaceutically acceptable" refers to a formulation of a compound that does not significantly abrogate the biological activity, a pharmacological activity and/or other properties of an active agent when the formulated compound is administered to a patient. In certain embodiments, a pharmaceutically acceptable formulation does not cause significant irritation to a patient.

To "treat" a disease as the term is used herein, means to reduce the frequency or severity of at least one sign or symptom of a disease or disorder experienced by a subject. Treating may include the postponement of further disease progression, or reduction in the severity of symptoms that have or are expected to develop, ameliorating existing symptoms and preventing additional symptoms. "Treat" a tumor means alleviating or eliminating the symptoms of a tumor, or slowing down the progression of the tumor. The alleviation is preferably at least about 10%, more preferably at least about 20%, 30%, 40%, 50%, 60%, 70%, 80%, 90% or 95%.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DETAILED DESCRIPTION

Embodiments of the materials and methods are described below.

It has been found that Zika virus effectively kills neural crest-derived tumor cells characterized by N-myc amplification, but not such cells lacking N-myc amplification. The cells having N-myc amplification also were discovered to express the marker, CD24 (also known as CD24A, signal transducer C24A; see e.g., GenBank FJ226006 for the nucleotide sequence and ACI46150.1 for the protein sequence and also GenBank NG_041768.1; see also L. Wang et al., "A dinucleotide deletion in CD24 confers protection against autoimmune diseases," *PLOS Genet.* 3 (4): E49, 2007).

Based on the clinical observation that Zika virus infections in children and adults are most often asymptomatic, wild-type or genetically modified or attenuated Zika viruses may be safely and effectively therapeutically administered to children or adults with tumors that express CD24 alone or also having N-myc-amplification. Even symptomatic patients have only mild disease marked by rash, fever, and conjunctivitis. Severe symptoms from Zika virus disease are rare.

The infecting Zika viruses will cause tumor lysis with little or no effect on normal host cells, providing a safe, effective, and novel means for treating these malignancies. It is believed that Zika viruses can be used to eliminate or reduce neural crest-derived tumors as well as other tumors expressing CD24 with minimal long term adverse effect.

CD24 positive tumors include ovarian cancer, colorectal cancer, B cell lymphomas, erythroleukemia, gliomas, small cell lung cancer, esophageal squamous cell carcinoma, hepatocellular carcinoma, cholangiocarcinoma, pancreatic adenocarcinoma, urothelial carcinoma, breast cancer, primary neuroendocrine carcinoma, and prostate carcinomas. Z. Fang et al., "CD24: From A to Z," Cell. & Mol. Immun. 7:100-13 (2010).

A Brazilian strain of Zika virus infection has been linked to major birth defects, including microcephaly in the babies of women who are pregnant at the time they are infected with the virus and has been tied to an increase to the number of cases of Guillain-Barré syndrome in adults. Fetal injury appears to be more likely when maternal infection occurs during the first trimester. Most later-pregnancy maternal Zika infections do not appear to result in an overtly injured infant.

The range of subjects treated with a composition comprising an oncolytic Zika virus (wild type or attenuated) includes pregnant females having a CD24 positive cancer, but excludes such patients in the first trimester of pregnancy. Also contemplated are compositions and methods of treating a pregnant woman who is believed to have been exposed to Zika virus or who resides in an area where Zika is prevalent with a neutralizing antibody or composition that will prevent Zika virus from interacting with CD24 as well as other high-risk immunocompromised individuals. Similarly, many CD24-expressing tumors (e.g., melanomas, ovarian carcinomas, gliomas, and glioblastomas) are resistant or refractory to currently available cancer treatments.

For treatment of neuroblastoma, patients receiving therapy are likely to be young children.

As is the case with any potential cancer therapy, the risks of Zika virus infection (which are minimal) must be balanced against both the toxicity and poor efficacy of current chemotherapy. If should be noted that N-myc-amplified neuroblastomas are more resistant to chemotherapy, and carry a worse prognosis; thus, a Zika virus therapy may be ideal for otherwise treatment-refractory tumors. It should also be noted that there is no known passive human-to-human transmission of Zika virus infection. While sexual intercourse and blood transfusions have been indicated as possible means of transmitting Zika virus, these modes of transmission are both avoidable and largely irrelevant in the treatment of children with neuroblastomas.

Following infection, an oncolytic Zika virus can kill a susceptible cancerous cell by direct lytic infection, induction of apoptosis or by initiating an immune response to viral antigens. The effect of the oncolytic virus is thus not limited to a single input dose. Susceptible cells can undergo a multi-cycle infection, resulting in the production of large numbers of progeny virus. These progeny virions can spread either locally to adjacent tumor cells, or systemically to distant metastatic sites. This feature of oncolytic therapy is particularly attractive for the treatment of inaccessible tumors or un-diagnosed micro-metastases.

Accordingly, a method for treating a neural crest-derived neoplasm in a subject is provided, by administration of an oncolytic Zika virus, where cells of the neoplasm are characterized by the expression of CD24. The subject may be a mammal, particularly one selected from the group consisting of dogs, cats, sheep, goats, cattle, horses, pigs, humans, and non-human primates. The mammal is preferably human.

Tumors treatable comprise those that are populated by tumor cells that are of embryonic neural crest origin or which express CD24. Neural crest-derived tumors include tumors of sympatho-adrenal lineage, which comprise neuroblastoma, paraganglioma and pheochromocytoma; tumors of melanocytes, i.e., melanomas; tumors of Schwann cell lineage including neurofibromas (type 1, also known as von Recklinghausen's disease; and type 2), malignant peripheral nerve sheath tumors, and schwannomas; and type A/B multiple endocrine neoplasias. For a discussion of neural crest-derived tumors, see Dundr, P. and Ehrmann, J., "Neuronal Crest Cell-Derived Tumors: An Overview", Chapter 4 in *Stem Cells and Cancer Stem Cells, Therapeutic Applications in Disease and Injury*: Volume 1, p. 29-40, M. A Hayat, ed., Springer Science+Business Media B.V., 2012.

Tumors that can be treated using the compositions and methods disclosed herein include tumors that are refractory to treatment with chemotherapeutics. The term "refractory", when used herein in reference to a tumor, refers to a tumor (and/or metastases thereof) that shows no or only weak anti-proliferative response (i.e., nor or only weak inhibition of tumor growth) after treatment with at least one chemotherapeutic agent. Thus, a refractory tumor cannot be treated at all or only with unsatisfying results with at least one (preferably standard) chemotherapeutic agent. Treatment of refractory tumors as mentioned is to be understood to encompass not only (1) tumors where one or more chemotherapeutics have already failed during treatment of a patient, but also (2) tumors that can be shown to be refractory by other means, e.g., biopsy and culture in the presence of chemotherapeutics and radiation treatment.

Subjects that can receive a treatment according to the present invention generally include any patient diagnosed with a neural crest-derived tumor or a tumor characterized as CD24 positive (CD24$^+$) tumor. The CD24 positive tumor may be selected from the group consisting of: an ovarian cancer, a colorectal cancer, a B cell lymphoma, erythroleukemia, a glioma, a small cell lung cancer, an esophageal squamous cell carcinoma, a hepatocellular carcinoma, a hepatoblastoma, a cholangiocarcinoma, a pancreatic adenocarcinoma, a melanoma, an urothelial carcinoma, a breast cancer, a primary neuroendocrine carcinoma, a neural crest-derived tumor, a human papillomavirus (HPV)-associated malignancy, an Epstein-Barr virus-induced malignancy, and a prostate carcinoma. The HPV-associated malignancy may be selected from the group consisting of cervical cancer or precancer, vaginal, vulvar, and anal precancers or cancers, and oropharyngeal precancers or cancers. An Epstein-Barr virus-induced malignancy may be selected from the group consisting of nasopharyngeal carcinoma, lymphoma, and post transplantation lymphoma proliferative disease.

Patients harboring CD24 positive tumors or who are at risk of developing such tumors are selected for Zika virus therapy on the basis of CD24 cells populating the tumor mass. Tumor cells may be assessed for the presence of CD24 using common histopathology methods.

For the determination of N-myc copy number in biopsied cells, N-myc copy numbers may be determined if needed by known molecular biological techniques. Southern blot analysis may be used to determine gene copy number. This typically involves extracting a significant quantity of genomic DNA, undergoing restriction digestions prior to blotting, followed by probing with labeled hybridization probes. Southern blot analysis is therefore laborious, time-consuming and requires considerable amounts of DNA from fresh or frozen samples. Southern blot assay-based determination of gene copy number has largely been supplanted by quantitative PCR (qPCR), including real-time RT-qPCR and fluorescence in situ hybridization (FISH). RT-qPCR is PCR visualized in real time by the use of fluorescent or intercalating dyes. Basic protocols for RT-qPCR gene copy number analysis are described, for example, by Ma et al., *Curr. Protoc. Hum. Genet.* (2014) 80: Unit 7.21 . . . doi: 10.1002/0471142905.hg0721s80. Gene copy number analyses may be carried out according to known protocols, e.g., utilizing commercially available equipment, e.g., SYBR Green I Dye Detection Protocol, Protocol 17 in *A Technical Guide to PCR Technologies*, Sigma-Aldrich Co. LLC., 2017, sigmaaldrich<dot>com/technical-documents/protocols/biology/sybr-green-i-dye-quantitative-pc<dot>html.

Additional methods of N-myc copy number analysis include fluorescence in situ hybridization FISH and RT-qPCR. FISH allows rapid and accurate determination of gene copy number, allows gene copy number evaluation at the single cell level and can be performed on tumor imprints of biopsies that can be evaluated for tumor cell morphology and content by combination with immunohistochemical staining. FISH may be employed for determination of N-myc copy number as described by Ambros, et al., *British Journal of Cancer* (2009) 100, 1471-1482).

A given tumor may contain a mixture of both CD24 positive and CD24 negative cells. Such tumors will also benefit from Zika virus oncolytic treatment since the eradication of the Zika-sensitive CD24 positive tumor cell may lead to tumor shrinkage and/or reduction in growth, thus resulting in some therapeutic benefit to the patient. Accordingly, the Zika virus oncolytic treatment may be carried out on tumors comprising both $CD24^+$ and $CD24^-$ cells, although greater anti-tumor response would occur in tumors comprising predominately $CD24^+$ tumor cells.

Zika virus has a positive-sense, single-stranded RNA genome approximately 11 kilobases (kb) in length. The genome contains 5' and 3' untranslated regions flanking a single open reading frame that encodes a polyprotein that is cleaved into three structural proteins: the capsid (C), pre-membrane/membrane (prM), and envelope (E), and seven non-structural proteins (NS1, NS2A, NS2B, NS3, NS4A, 2K, NS4B, and NS5). The Zika virus for use is an "oncolytic virus", that is, it is a virus that preferentially replicates in, and kills, neoplastic cells. Delivery of the oncolytic Zika virus to a neoplasm can result in substantial lysis of the neoplastic cells infected by the virus. The term "substantial lysis" means at least about 10% of the cells of a neoplasm are lysed. More preferably, at least about 20%, 30%, 40%, 50%, 60%, 70%, 80% or 90% of the cells are lysed. Most preferably, at least about 95% of the cells are lysed. The percentage of tumor cell lysis can be determined, for example, by measuring the reduction in the size of the tumor or reduction of symptoms of the tumor.

The Zika virus for administration may comprise naturally occurring (wild-type) Zika virus or modified Zika virus. The virus is "naturally occurring" when it can be isolated from a source (natural vector for the virus or an infected subject such as a human) in nature (or has been previously isolated from a natural source and stored in a biological depository).

A "modified" Zika virus is a Zika virus other than a naturally-occurring Zika virus. Accordingly, the term "Zika virus" as used herein refers to both a naturally-occurring and a modified virus, and encompass both Zika virus particles and naked Zika virus RNA.

The modified Zika virus is still capable of lytically infecting a target neoplastic cell of a host subject. For example, the genetic material of the virus may be mutated, or the virus particle may be modified. The modified virus may be a recombinant virus, for example a virus engineered to express a heterologous protein.

The virus may be modified by incorporation of mutated coat proteins, such as for example, into the virion capsid. The proteins may be mutated by replacement, insertion, or deletion. Replacement includes the insertion of different amino acids in place of the native amino acids. Insertions include the insertion of additional amino acid residues into the protein at one or more locations. Deletions include deletions of one or more amino acid residues in the protein. Such mutations may be generated by methods known in the art. For example, oligonucleotide site directed mutagenesis of the gene encoding for one of the coat proteins could result in the generation of the desired mutant coat protein. Expression of the mutated protein in virus infected mammalian cells in vitro such as COS 1 cells or Vero cells will result in the incorporation of the mutated protein into the virus virion particle.

The virus may be modified to reduce or eliminate an immune reaction to the virus. Such a modified virus is termed an "immunoprotected virus". Such modifications could include packaging of the virus in a liposome, a micelle, or other vehicle to mask the virus from the host immune system. For example, the virion may be treated with chymotrypsin in the presence of micelle-forming concentrations of alkyl sulfate detergents to generate a new infectious subvirion particle. Alternatively, the outer capsid of the virion particle may be removed since the proteins present in the outer capsid are the major determinant of the host humoral and cellular responses.

The virus may be a recombinant virus resulting from the recombination/reassortment of genomic segments from two or more genetically distinct viruses. Recombination/reassortment of virus genomic segments may occur in nature following infection of a host organism with at least two genetically distinct viruses. Recombinant virions can also be generated in cell culture, for example, by co-infection of permissive host cells with genetically distinct viruses.

It is preferable to avoid immune responses against the virus, particularly in animals that have previously received large amounts of the same virus or closely-related virus. Immune responses may be avoided if the virus is of a subtype or strain to which the mammal has not developed immunity or has not been vaccinated against.

While genetic modifications of the oncolytic Zika virus (that do not result in loss of oncolytic activity) may be carried out, modification may not be required from a safety standpoint. For example, the oncolytic Zika virus strain PRVABC59 (ATCC® VR-1843), utilized in the Examples, has no intended genetic modifications, although the virus has been passaged through and maintained in Vero cells, and as a consequence, may differ in RNA sequence from the originally-isolated virus. While longitudinal studies are ongoing to determine whether or not Zika virus infection in children and adults causes some subtle brain injury, nothing is yet reported. Zika virus infection in children and adults are generally asymptomatic in roughly 80% of individuals. Symptomatic cases or most often mild cases present with fever, rash, and conjunctivitis. Rarely, immunocompetent children and adults may develop Guillain-Barre syndrome, but direct causation of Guillain-Barre syndrome has not been proven, although the incidence of it has increased dramatically in Brazil which also has the greatest incidence of hydrocephalus in infants.

While attenuated Zika viruses may be considered for therapeutic use, the fact that 80% of Zika virus infections are asymptomatic, and the remaining 20% of infections are generally very mild, as well as the rarity of severe Zika virus disease, attenuation of Zika viruses for therapy may be unnecessary.

Moreover, since the anti-cancer effect of the Zika virus as demonstrated herein relies on virus-mediated lysis of target tumor cells, attenuation may adversely hinder the therapeutic effect of the virus. In general, genetically modified Flaviviruses are unstable and frequently nonfunctional, suggesting that native Zika viruses may be more suitable for therapeutic use.

Any suitable source of the oncolytic Zika virus may be used. The oncolytic activity of a candidate Zika strain for use may be determined by appropriate oncolytic assay, as described in the Examples that follow. For example, an N-myc-amplified neuroblastoma cell lines, e.g., IMR-32, SMS-KAN and SK-N-Be(1), or panel of such cell lines, is infected with the candidate Zika virus strain for oncolytic therapy, and cell toxicity can be determined by an appropriate proliferation assays. One such assay, known as the MTS assay, is a colorimetric method to determine the number of viable cells in proliferation or cytotoxicity assays toxicity assays. The test relies on an tetrazolium compound, MTS: [3-(4,5-dimethyl-2-yl)-5-(3-carboxymethoxyphenyl)-2-(4-sulfophenyl)-2H-tetrazolium, inner salt]. One such MTS assay is available from Promega Corp., Madison, WI as the CellTiter 96® AQueous One Solution Cell Proliferation Assay System.

A representative oncolytic assay test protocol comprises laying down $10^4$ N-myc-amplified neuroblastoma cells in a flat bottom 96-well tissue culture treated plated, and allowing the cells to attach overnight. The following day, cells are infected at an MOI (multiplication of infection, and refers to the number of virions that are added per cell during infection of the cell) of 10 with candidate Zika virus or left untreated (as controls). Cells are maintained at 37° C. and 5% $CO_2$. At time intervals following infection, the plates are examined using the CellTiter 96® AQueous One Solution Cell Proliferation (MTS) assay (Promega Corp, Madison, WI) according to the manufacturer's instructions. A loss of neuroblastoma cell viability indicates that the candidate Zika virus strain has oncolytic activity. The oncolytic activity of Zika virus strain PRVABC59 (ATCC® VR-1843), also known as "PR2015" was determined in this manner. PRVABC59 (ATCC® VR-1843) is available from American Type Culture Collection, 10801 University Boulevard, Manassas, Virginia, 20110.

Wild-type Zika strains that may be screened for oncolytic activity in this manner include, for example, the following strains commercially available from the American Type Culture Collection, 10801 University Boulevard, Manassas, Virginia, 20110: MR 766 (ATCC® VR84), originally isolated by Dick et al, *Trans R Soc Trop Med Hyg* 46:509-520, 1952; and an MR 766 tissue culture-adapted strain from ATCC® VR-84 (ATCC® VR-1838). The following Zika strains commercially available from BEI Resources, 10801 University Boulevard, Manassas, VA, 20110, a depository established by the National Institute of Allergy and Infectious Diseases (NIAID) and managed by ATCC, may likewise be screened for oncolytic activity: MR 766 (NR-50065); IbH 30656 (NR-50066); FLR (NR-50183); H/PAN/2016/BEI-259634 (NR-50210); H/PAN/2015/CDC-259359 (NR-50219); H/PAN/2015/CDC-259249 (NR-50220); H/PAN/2015/CDC-259364 (NR-50221); PRVABC59 (NR-50240); P 6-740 (NR-50245); MEX I-44 (NR-50279); DAK AR 41524 (NR-50338); R103451 (NR-50355); PLCal_ZV (NR-50234); MEX 2-81 (NR-50280); and MEX I-7 (NR-50281). The candidate virus may be one or more isolates from one or more species, including but not limited to avian, insect and mammalian species. An oncolytic Zika virus may be modified as described above to provide a modified Zika virus for administration, or the native unmodified virus may be administered.

PRVABC59 (ATCC® VR-1843) is an oncolytic Zika virus strain that can be used. It is an Asian-lineage Zika virus. Virus strains circulating in the Caribbean, and in Central and South America are Asian-lineage Zika viruses. Reports suggesting that African-lineage Zika virus strains are less neurotoxic than Asian-lineage Zika virus strains. Accordingly, Asian-lineage Zika virus strains are preferred, as they are likely to have increased lytic action in comparison to African-lineage Zika viruses. However, the oncolytic Zika virus strain selected for a patient should not be the same strain used in any eventual Zika virus vaccine administered to the patient, which could impact the oncolytic ability of that virus.

The oncolytic Zika virus may be administered to the subject in its native state, i.e., virus particles. Alternatively, the virus may be administered as naked viral nucleic acid, e.g., viral RNA, encoding the virus. Accordingly, unless indicated otherwise, "Zika virus" as used herein means other the native virus in the form of virus particles for naked Zika RNA. It should be appreciated that by "naked" viral RNA means RNA without the associated proteins that comprise a virus particle. Thus, "naked" viral RNA does not exclude RNA combined with formulation agents, such as liposome-forming agents, or other pharmaceutical vehicles. Naked viral RNA may be isolated from viral particles by known techniques, or may be synthetically made.

The naked viral RNA may be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolizable lipid capable of forming liposomes can be used. Compositions in liposome form may contain stabilizers, preservatives, excipients and the like. The preferred lipids are the phospholipids and the phosphatidyl cholines (lecithins), both natural and synthetic. Methods for forming liposomes are known in the art. See, Prescott, Ed., *Methods in Cell Biology*, Volume XIV, Academic Press, New York, N.Y. (1976), p. 33 et seq. In one exemplary embodiment, liposomes are formed with the cationic liposome formulation Lipofectamine™ 2000. Viral RNA: Lipofectamine™ 2000 complexes (vRNA: lipid) may be prepared according to manufacturer's instructions (Thermo Fisher Scientific Inc.). Briefly, various amounts of vRNA and 2 μl Lipofectamine™ 2000 can be diluted separately in 50 μl serum and antibiotic free media and gently mixed. Five minutes following Lipofectamine™ 2000 dilution, the corresponding vRNA and lipid solutions can be combined and gently mixed. The mixture is incubated at room temperature for 45 minutes to allow vRNA: lipid complexes to form. Once formed, the complexes can be administered to the subject in need of cancer treatment for a $CD24^+$ tumor.

The therapeutic agent may comprise a single species of oncolytic Zika viruses. Alternatively, a combination of at least two oncolytic Zika viruses may be administered. The viruses may be administered at the same time, by the same route, or at different times, by different routes.

The oncolytic Zika virus is administered to a subject in a manner that results in contact of the virus with target neoplastic cells. The route by which the virus is administered, as well as the formulation, carrier or vehicle, will depend on the location as well as the type of the neoplasm. A wide variety of administration routes can be employed. For example, for a solid neoplasm that is accessible, the virus can be administered by injection directly to the neoplasm. For neoplasms that are not easily accessible within the body, such as metastases or brain tumors, the virus can be administered in a manner such that it can be transported systemically through the body of the mammal and thereby reach the neoplasm (e.g., intravenously, or intramuscularly).

Because neuroblastomas may be metastatic to many sites (including bone marrow), local/intratumor administration may or may not be effective. Zika virus may be administered intradermally, subcutaneously, or intravenously, with the anticipation that the patient will become transiently viremic, with the consequent hematogenous delivery of virus to the tumor.

In such cases, viruses that are administered systemically, i.e., by intravenous injection, will spread to the locations of the neoplastic cells, resulting in lysis of the cells. Brain metastases occur in patients with Stage IV neuroblastoma, and in patients with relapsed neuroblastoma (Zhu et al., Chin. J. Cancer 2015 34:49). The ability of Zika virus to cross the blood brain barrier (BBB) could be beneficial in cases of neuroblastoma metastatic to the brain.

Alternatively, the virus can be administered directly to a single solid neoplasm, where it then is carried systemically through the body to metastases. The virus can also be administered topically, e.g., for melanoma. The virus can be administered systemically to mammals which are immune compromised or which have not developed immunity to the virus. More than one route of administration may be used to deliver the oncolytic Zika virus.

In certain embodiments, the oncolytic virus is delivered by direct injection to a tumor (e.g., intralesional injection), or by systemic administration. Intralesional injection of a tumor may be performed by any appropriate means known to the skilled person, taking into account factors such as the type of tumor being treated, the size and location of the tumor, accessibility of the tumor to direct injection. Injection techniques that increase or maximize the distribution of the virus throughout the tumor may offer improved therapeutic outcomes. For example, in the treatment of melanoma and other solid tumors, multiple lesions may be injected in a dose hyper-fraction pattern, starting with the largest lesion(s) (2.0 mL injected into tumors >2.5 cm, 1.0 mL into 1.5 to 2.5 cm; 0.5 mL into 0.5 to 1.5 cm) to a 4.0 mL maximum.

Direct administration to the brain (or to a specific region of the brain) may be achieved, for example, and not by way of limitation, by local infusion (e.g., during surgery), by injection (e.g., intracerebroventricular injection), by means of a catheter, or by means of a ventricular reservoir or pump placed in the tumor cavity during surgery or implanted subcutaneously in the scalp and connected to the brain via an outlet catheter. Alternatively or additionally, local administration can be achieved via the use of an implant device (e.g., a wafer implant containing the active ingredient) or a drug depot that can be placed locally during surgery. Such systems provide sustained oncolytic virus release.

Since neuroblastomas can be widely metastatic, intratumor injection is not likely to be an effective therapy for most neuroblastoma patients, unless there is a subsequent systemic dissemination of virus.

Before, during or after the administration of the oncolytic Zika virus, the subject may be given an immunosuppressive therapy to facilitate or enhance the effect of the virus treatment. The immunocompetency of the subject of the oncolytic Zika virus treatment may be suppressed by an immunosuppressive therapy comprising the co-administration (or prior or subsequent) administration of pharmaceuticals known in the art to suppress the immune system in general or alternatively by administration of anti-idiotypic antibodies that recognize the antibodies for the administered virus.

The oncolytic Zika virus may be administered to immunocompetent mammals in conjunction with the administration of immunosuppressants and/or immunoinhibitors. Such immunosuppressants and immunoinhibitors are known to those of skill in the art and include but are not limited to such agents as cyclosporin, rapamycin, tacrolimus, mycophenolic acid, azathioprine and their analogs, and the like. Other agents are known to have immunosuppressant properties as well (see, e.g., GOODMAN AND GILMAN, 7th Edition, page 1242).

Such immunoinhibitors also include anti-antivirus antibodies, which are antibodies directed against anti-virus antibodies that specifically recognize the virus of interest. Such antibodies can be made by methods known in the art. See for example *Antibodies: A laboratory Manual*, E. Harlow and D. Lane, Cold Spring Harbor Laboratory, 1988). Such anti-antivirus antibodies may be administered prior to, at the same time, or shortly after the administration of the virus. Preferably an effective amount of the anti-antivirus antibodies are administered in sufficient time to reduce or eliminate an immune response by the mammal to the administered virus.

The humoral immunity of the mammal against virus may also be temporarily reduced or suppressed by plasmapheresis of the mammal's blood to remove antibodies specific for that virus. The humoral immunity of the mammal against the virus may additionally be temporarily reduced or suppressed by the intravenous administration of non-specific immunoglobulin to the mammal. The immune system may also be suppressed by anti-CD4 and/or anti-CD8 antibodies, or complement neutralization.

Zika viruses may be grown to high titer in Vero cells. Vero cells are a commercially available immortal cell like derived from the kidney of an African Green Monkey. Vero cells are commonly used for the expansion of viruses. Zika virions may be purified by ultrafiltration and/or by gradient sedimentation, according to known techniques.

The oncolytic Zika virus may be purified for therapeutic administration by standard methodology. As used herein, "purified viruses" refer to viruses that have been separated from cellular components that naturally accompany them. Typically, viruses are considered purified when they are at least 70% (e.g., at least 75%, 80%, 85%, 90%, 95%, or 99%) by dry weight, free from the proteins and other cellular components with which they may be naturally associated.

The oncolytic Zika virus may be formulated appropriately for pharmaceutical administration. Pharmaceutical compositions comprises one or more oncolytic Zika viruses and a pharmaceutically acceptable carrier. A pharmaceutically acceptable carrier can be a solid, semi-solid, or liquid material that can act as a vehicle, carrier or medium for the virus. For infusion, particularly intravenous infusion, the virus may be formulated in an aqueous solution of mineral salts or other water-soluble molecules, e.g., normal saline, a solution of sodium chloride at 0.9% concentration; Ringer's lactate or Ringer's acetate; or a solution of 5% dextrose in water ("D5W"). Pharmaceutical compositions can be formulated to provide quick, sustained or delayed release of a virus after administration by employing procedures known in the art. Various other formulations for use in a pharmaceutical composition can be found in *Remington, The Science and Practice of Pharmacy* 22nd ed., Loyd V. Allen et al, editors, Pharmaceutical Press (2013). The oncolytic Zika virus may be administered topically, particularly for the treatment of melanoma, in the form of a gel, ointment or other semi-solid formulation, for example. The virus may be contained in a transdermal device to provide continuous or discontinuous virus delivery. The construction and use of transdermal patches for the delivery of pharmaceutical agents is known in the art. See, for example, U.S. Pat. No. 5,023,252. Such patches can be constructed for continuous, pulsatile, or on-demand delivery of viruses.

The oncolytic Zika virus is administered to a subject in need of such treatment in an amount that is sufficient to treat the neoplasm. A neoplasm is treated when administration of virus to the proliferating cells effects lysis of the proliferating cells. This may result in a reduction in size of the neoplasm or a complete elimination of the neoplasm. The reduction in size of the neoplasm, or elimination of the neoplasm, is generally caused by lysis of neoplastic cells by the virus. Preferably the effective amount is that amount able to at least inhibit tumor cell growth. Preferably the effective amount is from about 1 pfu/kg body weight to about $10^{15}$ pfu/kg body weight, and more preferably from about 100 pfu/kg body weight to about $10^{13}$ pfu/kg body weight. For example, for treatment of a human subject, approximately 100 to $10^{17}$ pfU of virus can be used, depending on the type, size, location and number of tumors present. The effective amount will be determined on an individual basis and may be based, at least in part, on consideration of the type of virus; the chosen route of administration; the individual's size, age, gender; the severity of the patient's symptoms; the size and location or other characteristics of the neoplasm; and the like. Given that Zika viruses are transmitted in nature by mosquitos at very low concentration, dosages of less than 100 pfU may be possible.

Treatment efficacy may be assessed both by tumor size and based upon biochemical markers, such as homovanillic acid (HVA) and vanillylmandelic acid (VMA). Elevated values of HVA, and VMA, and other catecholamine metabolites, are markers for the presence of suggestive of the presence of neural crest tumors, particularly neuroblastoma.

Because of the likely development of humoral immunity, an initial course of treatment an initial treatment course is likely to be limited to, e.g., five days in the absence of steps taken temporarily reduce or suppress patient humoral immunity.

The compositions are preferably formulated in a unit dosage form, each dosage containing from about $10^2$ pfu to about $10^{13}$ pfu of virus. The term "unit dosage forms" refers to physically discrete units suitable as unitary dosages for human subjects and other mammals, each unit containing a predetermined quantity of virus calculated to produce the desired therapeutic effect, in association with a suitable pharmaceutical excipient.

A stock of the oncolytic Zika virus composition may be diluted to an appropriate volume suitable for dosing, for example to achieve the desired dose of viral particles administered in a desired volume. The volume in which the virus is administered will be influenced by the manner of administration. For example, intravenous administration of virus may typically use about 5 ml to about 500 ml of virus diluted in normal saline, infused by an automatic pump over approximately 30 minutes.

Dosages of oncolytic Zika virus vary and are administered in one or more dose administrations, for example, daily, for one or several days. The virus is administered in a single dose or in multiple doses (e.g., two, three, four, six, or more doses). The multiple doses can be administered concurrently, or consecutively. The virus can also be administered to more than one neoplasm in the same individual. The virus may be administered, for example, continuously to a subject at least once per day or up to intermittently or continuously throughout the day on consecutive days, for a period of time.

Because the patient will become viremic in response to Zika virus administration, the patient will mount a humoral and cellular response that is likely to be neutralizing, within 5-10 days of first administration. Such a virus-neutralizing response will render further virus administrations ineffective, unless Zika viruses with capsids that express divergent epitopes are used in subsequent administrations, or steps are taken to reduce or suppress the patient immune response.

In certain embodiments, the virus is administered, for example, to subjects by means of intravenous administration in any pharmacologically acceptable solution, or as an infusion over a period of time. For example, the substance may be administered systemically by injection, or administered by infusion in a manner that results in the daily delivery into the tissue or blood stream of the subject. Where the administration is by infusion, the infusion can be a single sustained dose or can be delivered by multiple infusions.

The oncolytic Zika virus-based treatment may be combined with other anti-neoplasm treatment modalities, such as chemotherapy (with another chemotherapeutic agent active agent other than an oncolytic Zika virus), radiotherapy, surgery, hormone therapy and/or immunotherapy. For example, the virus may be administered in conjunction with surgery or removal of the neoplasm. Administration of virus at or near to the site of the neoplasm can be combined with surgical removal. The oncolytic Zika virus may be administered in conjunction with or in addition to radiation therapy. The oncolytic Zika virus may be administered in conjunction with or in addition to one or more anti-cancer agents, also known as "chemotherapeutic agents". These terms refer to those medications that are used to treat cancer or cancerous conditions. Anti-cancer drugs are conventionally classified in one of the following group: alkylating agents, purine antagonists, pyrimidine antagonists, plant alkaloids, intercalating antibiotics, aromatase inhibitors, anti-metabolites, mitotic inhibitors, growth factor inhibitors, cell cycle inhibitors, enzymes, topoisomerase inhibitors, biological response modifiers, anti-hormones and anti-androgens. Examples of such anti-cancer agents include, but are not limited to, BCNU, cisplatin, gemcitabine, hydroxyurea, taxanes (e.g., docetaxel, paclitaxel), temozomide, topotecan, fluorouracil, vincristine, vinblastine, procarbazine, decarbazine, altretamine, methotrexate, mercaptopurine, thioguanine, fludarabine phosphate, cladribine, pentostatin, cytarabine, azacitidine, etoposide, teniposide, irinotecan, docetaxel, doxorubicin, daunorubicin, dactinomycin, idarubicin, plicamycin, mitomycin, bleomysin, tamoxifen, flutamide, leuprolide, goserelin, aminogluthimide, anastrozole, amsacrine, asparaginase, mitoxantrone, mitotane, and amifostine.

Methods of the present invention can also be employed together with one or more further combinations of cytotoxic agents as part of a treatment regimen, wherein the further combination of cytotoxic agents is selected from: CHOPP (cyclophosphamide, doxorubicin, vincristine, prednisone, and procarbazine); CHOP (cyclophosphamide, doxorubicin, vincristine, and prednisone); COP (cyclophosphamide, vincristine, and prednisone); CAP-BOP (cyclophosphamide, doxorubicin, procarbazine, bleomycin, vincristine, and prednisone); m-BACOD (methotrexate, bleomycin, doxorubicin, cyclophosphamide, vincristine, dexamethasone, and leucovorin); ProMACE-MOPP (prednisone, methotrexate, doxorubicin, cyclophosphamide, etoposide, leucovorin, mechloethamine, vincristine, prednisone, and procarbazine);

ProMACE-CytaBOM (prednisone, methotrexate, doxorubicin, cyclophosphamide, etoposide, leucovorin, cytarabine, bleomycin, and vincristine); MACOP-B (methotrexate, doxorubicin, cyclophosphamide, vincristine, prednisone, bleomycin, and leucovorin); MOPP (mechloethamine, vincristine, prednisone, and procarbazine); ABVD (adriamycin/doxorubicin, bleomycin, vinblastine, and dacarbazine); MOPP (mechloethamine, vincristine, prednisone and procarbazine) alternating with ABV (adriamycin/doxorubicin, bleomycin, and vinblastine); MOPP (mechloethamine, vincristine, prednisone, and procarbazine) alternating with ABVD (adriamycin/doxorubicin, bleomycin, vinblastine, and dacarbazine); ChlVPP (chlorambucil, vinblastine, procarbazine, and prednisone); IMVP-16 (ifosfamide, methotrexate, and etoposide); MIME (methyl-gag, ifosfamide, methotrexate, and etoposide); DHAP (dexamethasone, high-dose cytaribine, and cisplatin); ESHAP (etoposide, methylpredisolone, high-dose cytarabine, and cisplatin); CEPP (B) (cyclophosphamide, etoposide, procarbazine, prednisone, and bleomycin); CAMP (lomustine, mitoxantrone, cytarabine, and prednisone); CVP-1 (cyclophosphamide, vincristine, and prednisone), ESHOP (etoposide, methylprediso-lone, high-dose cytarabine, vincristine and cisplatin); EPOCH (etoposide, vincristine, and doxorubicin for 96 hours with bolus doses of cyclophosphamide and oral prednisone), ICE (ifosfamide, cyclophosphamide, and etoposide), CEPP (B) (cyclophosphamide, etoposide, procarbazine, prednisone, and bleomycin), CHOP-B (cyclophosphamide, doxorubicin, vincristine, prednisone, and bleomycin), CEPP-B (cyclophosphamide, etoposide, procarbazine, and bleomycin), and P/DOCE (epirubicin or doxorubicin, vincristine, cyclophosphamide, and prednisone).

As will be appreciated by one skilled in the art, the selection of one or more therapeutic agents to be administered in combination with a method of treatment of the present invention will depend on the tumor of neural crest origin to be treated.

Combinations of the oncolytic Zika virus and chemotherapeutic agents are administered either concomitantly (e.g., as an admixture), separately but simultaneously (e.g., via separate intravenous lines into the same subject), or sequentially (e.g., one of the compounds or agents is given first followed by the second). Thus, the term "combination" is used to refer to concomitant, simultaneous, or sequential administration of two or more agents.

In one embodiment, oncolytic Zika virus is administered for the management of minimal residual disease, particularly neuroblastoma. In this case, the disease is not amenable to surgical treatment, and, in most cases, patients will have already received chemical cancer chemotherapy such that the remaining tumor cells may be drug-resistant. Because Zika viruses would be administered systemically with hematogenous delivery of virus to tumor cells, Zika viruses may be an effective means for treating minimal residual disease.

The interaction between a virus and its cellular receptor(s) is important for the determination of viral tissue and host tropisms. For instance, viral infection may be blocked by a viral-receptor binding protein. Accordingly, a viral cell receptor, and the viral molecule(s) that bind the receptor, are promising targets for developing anti-viral strategies. As demonstrated herein, human CD24, a cell surface glycoprotein, has been identified as a part of the Zika virus host cell entry pathway. The identification of a cell surface receptor for Zika virus enables a focused strategy to, for instance, identify the CD24-binding molecule(s) of Zika virus. For instance, preparing anti-Zika virus antibodies that specifically block binding to CD24 provides a handle to identify the Zika virus CD24-binding molecule(s). The viral CD24-binding molecule(s) is a candidate as an effective vaccine antigen. It is worth noting that Zika virus tends to mutate fast. However, given the strong selective pressure presented by CD24 binding being a part of viral entry into a host cell, it is not unreasonable to expect that the portion of the viral molecule(s) that binds CD24 is less likely to mutate. Therefore, identifying the viral CD24-biding molecule is a promising avenue for obtaining effective vaccine antigens.

Additionally, developing anti-human CD24 antibodies that block Zika virus binding to CD24 are also useful. For instance, an anti-CD24 antibody (monoclonal antibodies or fragments thereof such as Fab, scFv, F(ab')$_2$, and domain antibodies) that blocks Zika virus binding to CD24 is a candidate as prophylactic therapeutics for persons at risk of Zika virus exposure. An anti-CD24 antibody that blocks Zika virus binding to CD24 may also be useful in screening small molecule libraries for candidate molecules that block Zika virus binding to CD24. Such molecules are also candidates as prophylactic therapeutics for persons at risk of Zika virus exposure.

The practice of the invention is illustrated by the following non-limiting examples.

EXAMPLES

An Array of Neuroblastoma Cells are Permissive to Zika Virus Infection

Six human neuroblastoma cell lines (including 3 MYCN-amplified and 3 non-MYCN-amplified) along with Vero cells (a control cell line) were infected with Zika virus (strain=PR2015) at an MOI=10. The cells were allowed to incubate for a total of 10 days, with samples acquired every two days (starting with Day 0). Acquired cell samples were screened for cell viability (by MTS assay) and compared to uninfected cells (FIG. 1).

The results indicate that the three MYCN-amplified cell lines (i.e., IMR-32, SMS-KAN, and SK-N-Be (1) cells) all showed losses in cell viability that surpassed even the Vero control cells. Of the non-MTCN-amplified cells, only CHLA-42 showed a strong response to infection. Surprisingly, the non-MYCN-amplified cell line SK-N-AS not only did not succumb to Zika infection, but actually recovered after only a slight dip in cell viability. Overall, these observations indicate that a phenotypic range of neuroblastoma cells are susceptible to Zika virus infection, independent of MYCN amplification.

Figure 2:
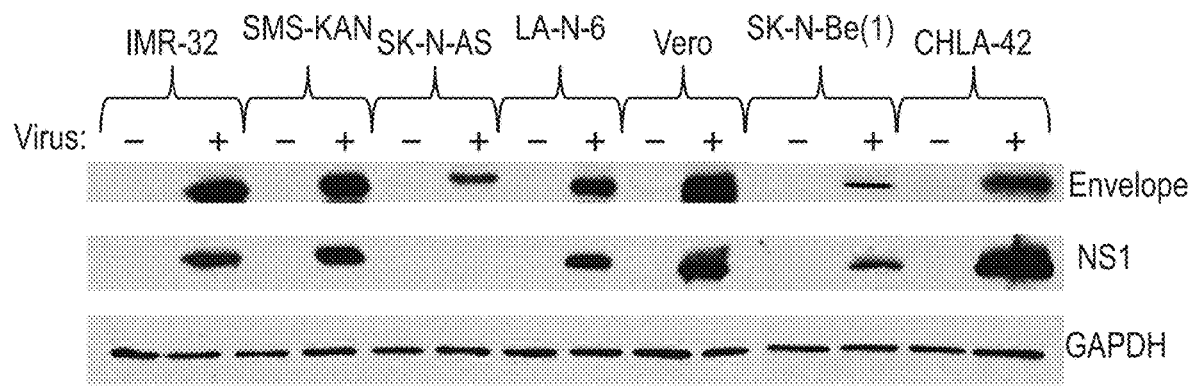
FIG. 2 depicts Western blot analysis of Zika virus infections in human neuroblastoma cells (compared to Vero cell control). Analysis was performed for Zika envelope protein and NS1 (Non-Structural 1) protein compared to GAPDH control.

Neuroblastoma Cell Lines Tested were Permissive of Zika Virus Infection, with the Exception of SK-N-AS Cells Zika virus binding to exposed cells was examined by demonstrating the presence of cell-associated viral envelope protein. Because the NS1 protein is not expressed until early in the course of infection, Zika virus infection was inferred by demonstration of de novo synthesis of the Zika virus NS1 protein. In these experiments, neuroblastoma cell lines were infected with an MOI=10 of Zika virus particles for four days. At the time of harvest, the culture medium was removed and cells were thoroughly washed in PBS to remove residual virus particles. Total cellular protein was extracted and the viral envelope and NS1 proteins were analyzed by Western blot (FIG. 2). Western blot analysis of the cell lines after infection revealed that all the cell lines showed evidence of the presence of the Zika envelope protein (Env), confirming that virus had been introduced and attached to the cell surface. However, a comparison of the NS1 protein levels indicated that all cells expressed detectable levels, with the exception of SK-N-AS cells, that showed no detectable levels of NS1 expression. This data suggested that SK-N-As cells might be missing a necessary receptor or surface cofactor necessary for viral uptake.

Figure 3:
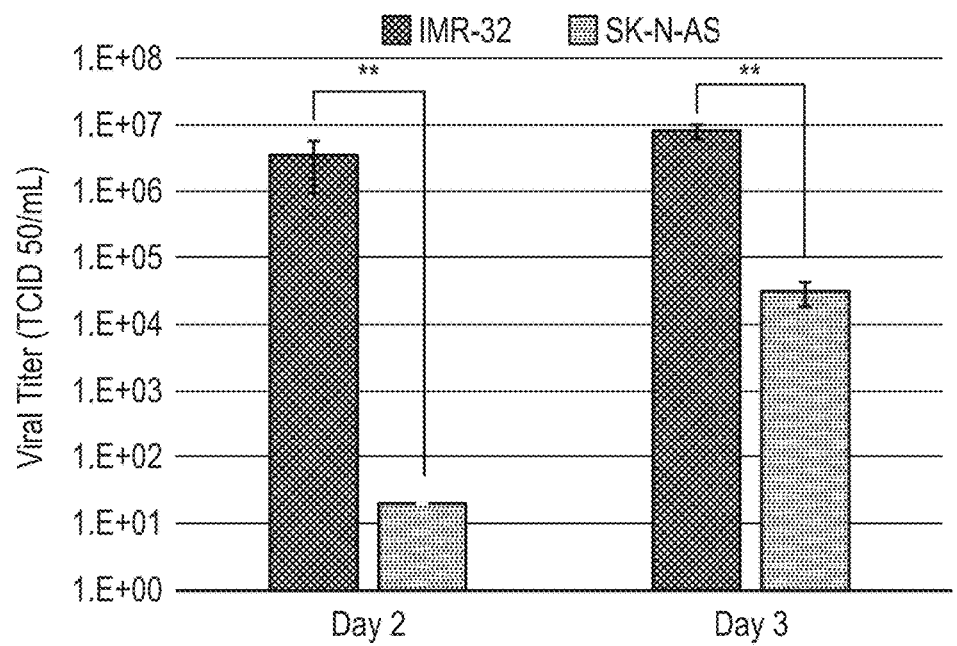
FIG. 3 depicts results of viral titer (TCID50) assays of IMR-32 and SK-N-AS cells at day 2 and day 3 post-infection. Data is composed of three biological replicates examined in sextuplicate, with error bars representing standard deviation. ** $p<0.05$, Student's t-test.
Figure 4A:
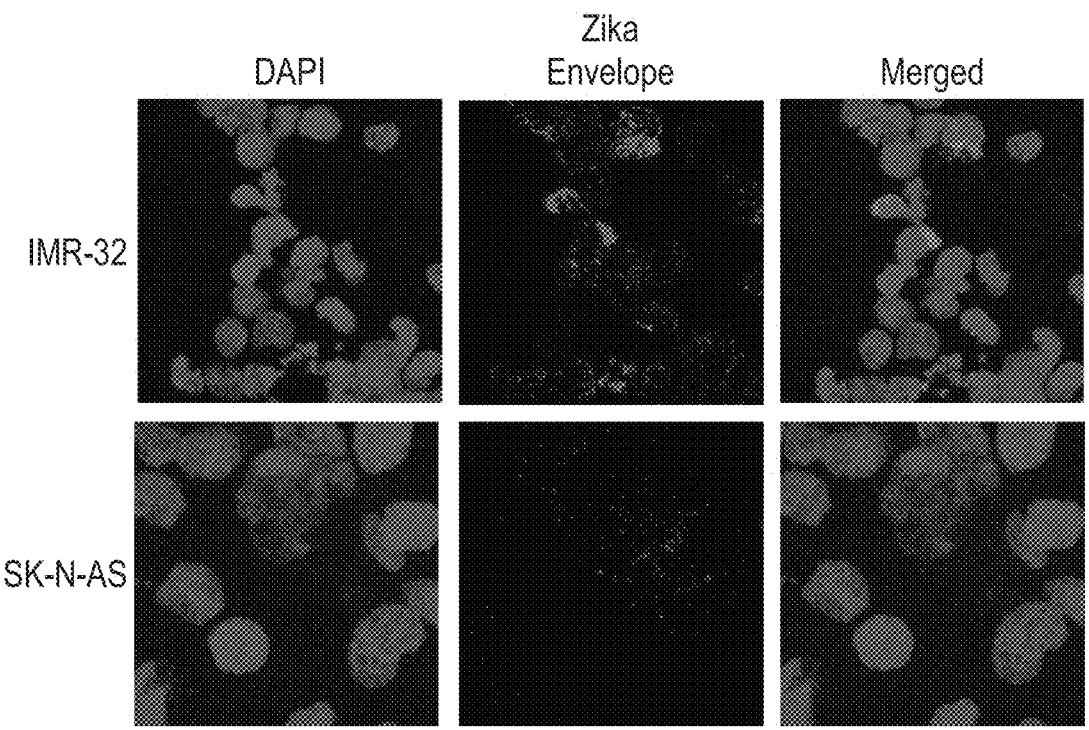
FIGS. 4A and 4B depict immunofluorescence labeling of Zika viral Envelope protein in neuroblastoma cells.
Figure 4B:
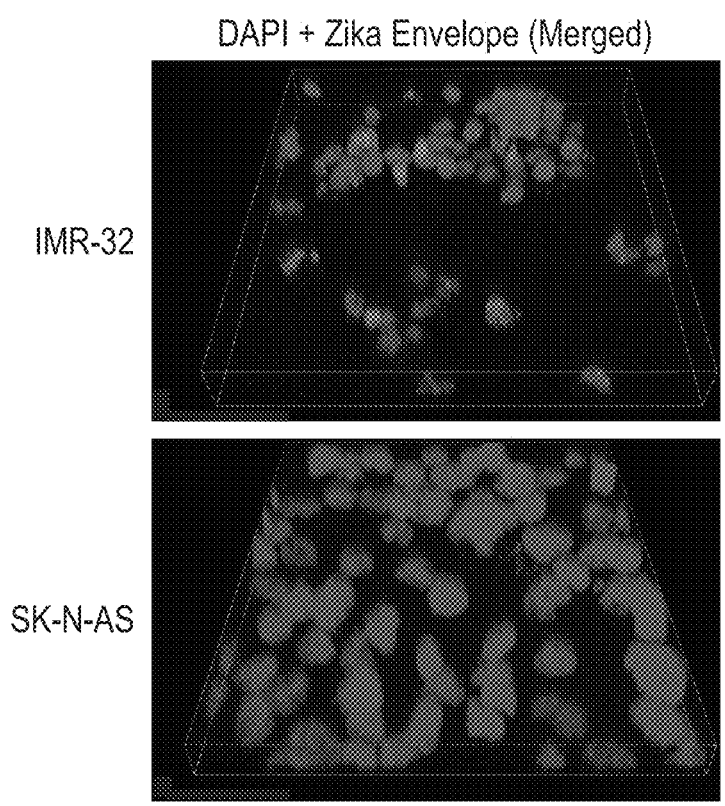

To determine whether SK-N-AS cells were permissive to Zika viral infection, the culture media viral titers of infected SK-N-AS cells to IMR-32 cells were compared at 2-days and 3-days post-infection (FIG. 3). Viral titer (50% Tissue culture Infective Dose (TCID50)) assays confirmed that both cells lines produce active virus; however, viral yields from IMR-32 cells were 5 orders of magnitude greater than SK-N-AS cells ($3 \times 10^6$ versus $2 \times 10^1$) at Day 2 post-infection and remained between 2-3 orders of magnitude greater by Day 3 post-infection ($8 \times 10^6$ versus $3 \times 10^4$). In addition, although immunofluorescent labeling of Zika Envelope protein was robustly detected in IMR-32 cells, the abundance of Envelope protein could barely be confirmed in SK-N-AS cells (FIG. 4A), suggesting that the lack of NS1 detection by western blot may have been due to a limit in the sensitivity of the assay due to the poor production of the virus in these cells. Regardless, 3-dimensional Zstacks confirmed the presence of Envelope protein primarily in the cytoplasm of in IMR-32 cells (FIG. 4B). Together, these data indicate that, while Zika virus appears capable of infecting all of the neuroblastoma cell lines tested, SK-N-AS are far less permissive to Zika virus infection, but are still capable of producing low-levels of active virus.

Permissive Zika Virus Infection in Neuroblastoma Cells Directly Correlates with CD24 Expression Given the above data, Zika virus particles bound to all cell types tested but caused a poorly productive infection in SKN-AS cells. To determine why Zika virus produced such a poor infection in SK-N-AS cells, the global transcriptomes were compared between the poorly productive SK-N-AS cells and the highly productive IMR-32 cells. It was hypothesized that neuroblastoma cell permissivity to Zika virus infection would correlate with expression of a membrane-associated protein. Analysis of global transcriptomics by Next Gen sequencing suggested possible differentially expressed genes that might serve as down-regulated receptors. One such gene, CD24, was selected for further analysis. CD24 is a GPI-linked surface glycoprotein expressed in differentiating neuroblasts and B lymphocytes (Hough et al, 1994, doi: 10.1006/geno.1994.1356) and is known to be crucial for neuronal development (Gilliam et al., 2017, doi: 10.1016/j.nbd.2016.12.011).

Figure 5A:
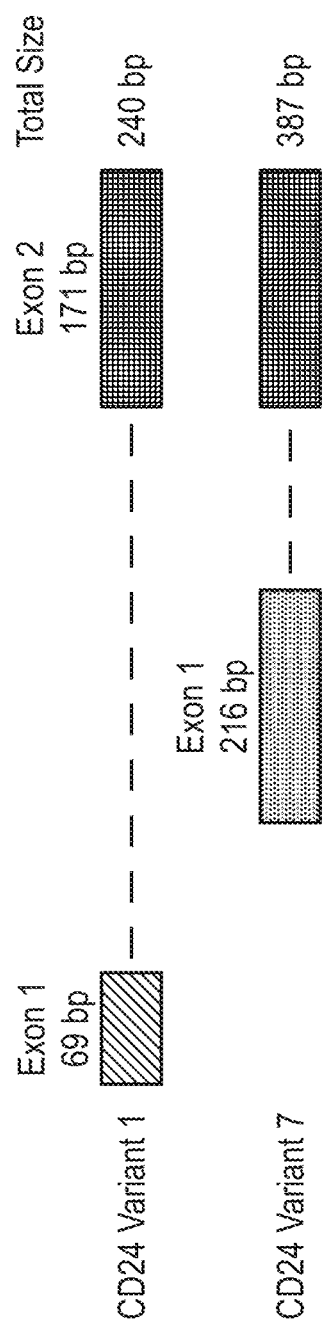
FIGS. 5A, 5B, 5C, 5D, and 5E depict analysis of CD24 expression in human neuroblastoma cells.
Figure 5B:
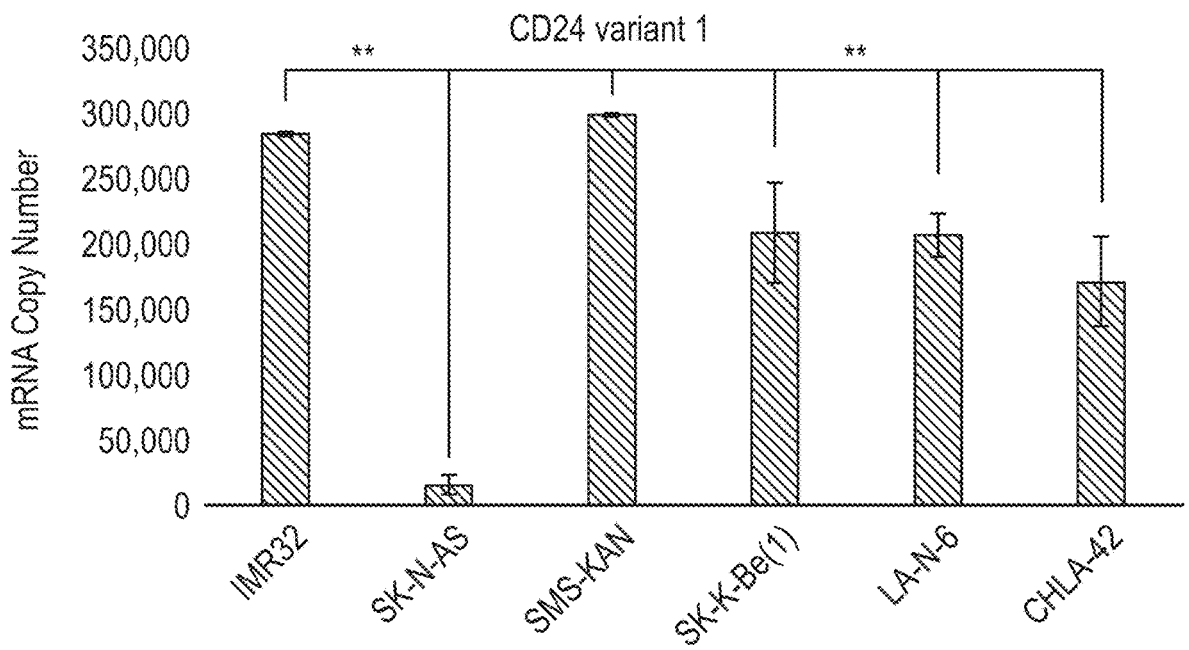
Figure 5C:
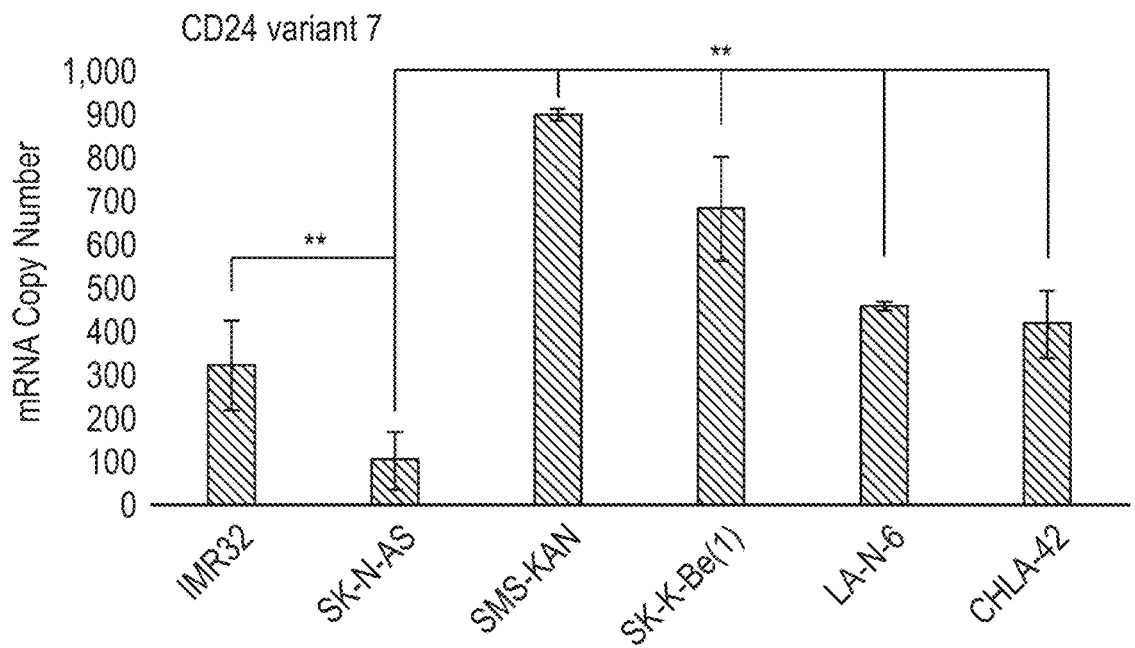
Figure 5D:
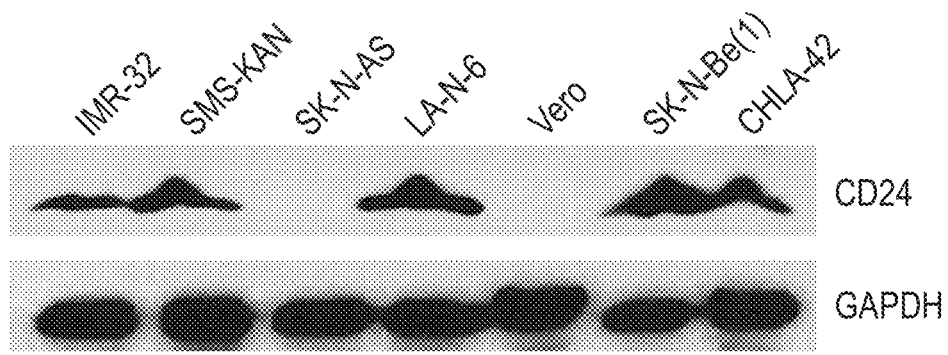

An analysis of the CD24 transcripts revealed three separate transcripts, all of which were significantly higher expressed in IMR-32 cells than in SK-N-AS cells. The three transcripts encode two distinct open reading frames, two of the transcripts (NM_013230 & NM_001291738) having the same open reading frame, whereas transcript NM_001291739 utilizes an alternate first exon. Both ORFs utilize the same sequence in their second exon. The two splice variants were identified as variant-001 and variant-007 (FIG. 5A). To determine if these CD24 splice variants were expressed in other neuroblastoma cell lines, an absolute quantification of mRNA transcripts was performed using quantitative real-time PCR (qRT-PCR) (FIGS. 5B and 5C). The results revealed that both CD24 splice variant-001 and variant-007 mRNA transcripts were highly expressed in nearly all neuroblastoma cell lines tested, with the exception of the SK-N-AS cells; in SK-N-AS cells, the CD24 splice variants were expressed at very low levels. CD24 expression was validated by western blot analysis of whole cell lysates (FIG. 5D). CD24 protein was easily detected in all neuroblastoma cell lines screened, except SK-N-AS cells, in which no CD24 protein was detectable.

Figure 5E:
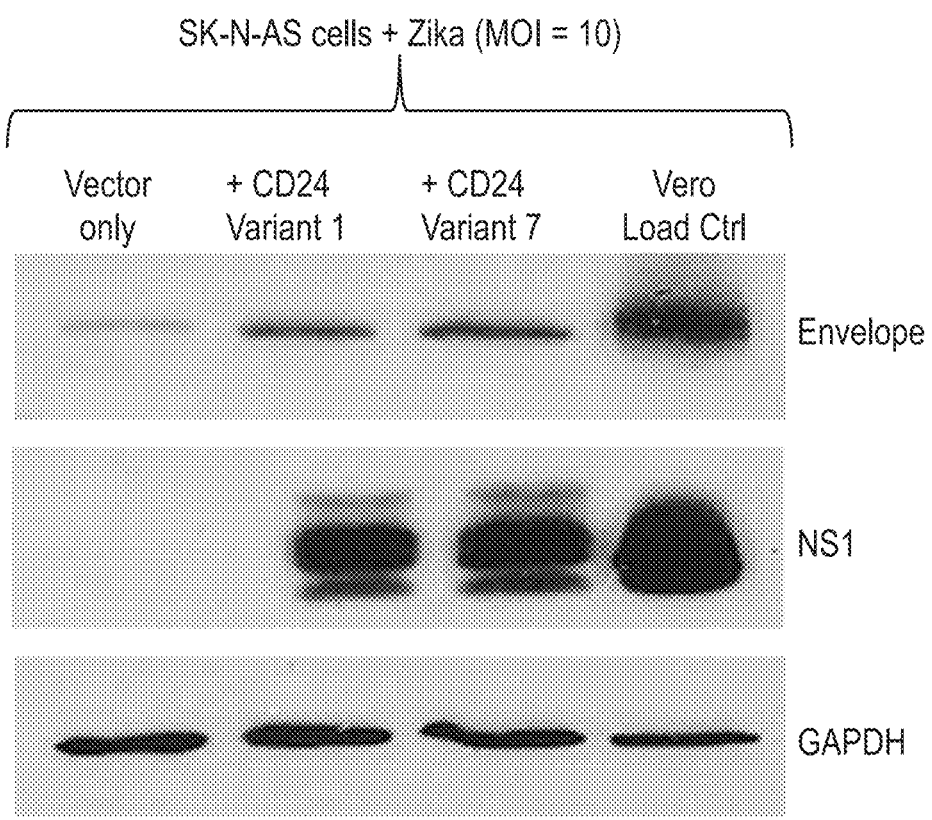

CD24 was cloned from IMR-32 cells and recombinant expression vectors were constructed containing two possible splice variants (variant-001 and variant-007). These expression plasmids were transiently transfected into SK-N-AS cells for 48 hours (along with vector only control cells and Vero cells), after which the cells were infected with Zika virus (MOI=10) and incubated for 4 additional days. The samples were then analyzed by Western blot (FIG. 5E). The results indicated that the transient expression of CD24 increased the amount of Zika envelope protein present, but most dramatically increased the presence of Zika NS1 protein (indicating a productive infection in these cells).

Figure 6A:
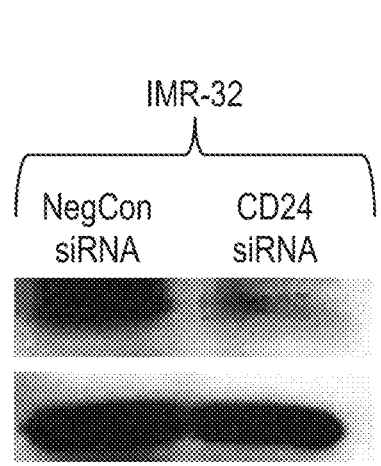
FIGS. 6A and 6B depict the role of CD24 in Zika-virus infected neuroblastoma cells.
Figure 6B:
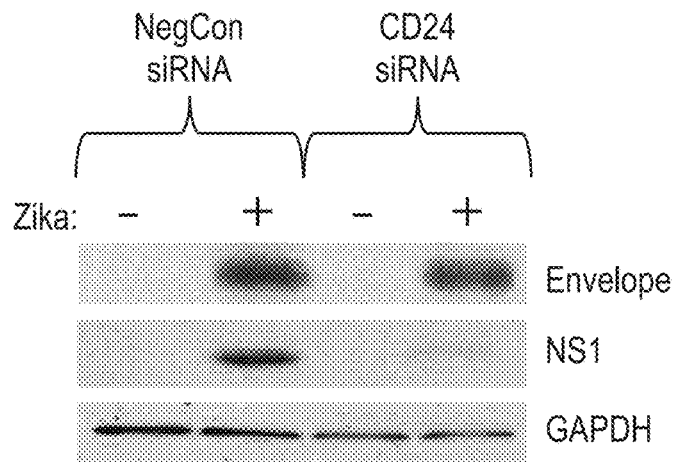

CD24 Expression is Necessary for the Production of NS1 Protein in Neuroblastoma Cells Infected with Zika Virus It is worth noting that Vero cells do not express CD24 (FIG. 5D), suggesting that an alternate factor may be present in these cells which allows for productivity. Vero cells are derived from epithelial kidney cells of the African green monkey and are not of neuronal cell lineage. Therefore, it would not be predicted that CD24 be expressed in these cells. However, these data do indicate that CD24 may be necessary for productive infections in neuroblastoma cells. To validate this hypothesis, IMR-32 cells were transfected with siRNAs specific to CD24. The knockdown of CD24 was validated compared to Negative Control siRNA 48 hours after transfection by Western blot analysis (FIG. 6A). These cells were then split, with each sample either infected with Zika virus (MOI=10) or left uninfected (FIG. 6B). An analysis of these samples indicated that the loss of CD24 in IMR-32 cells did effect the production of Zika NS1 protein, leading to a dramatic drop in content. These data support the hypothesis that CD24 may be necessary for a productive infection in neuroblastoma cells.

Figure 7:
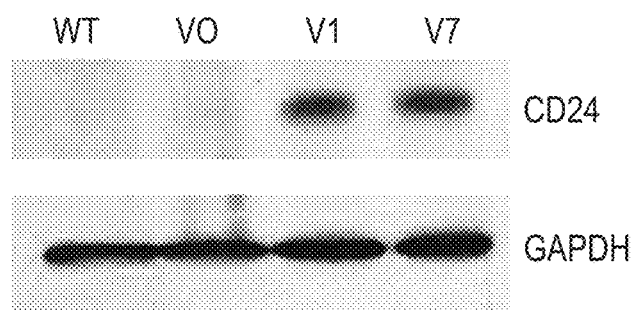
FIG. 7 depicts a Western blot of stable CD24 expression in SK-K-AS cells as compared to wild-type and vector only controls.
Figure 8:
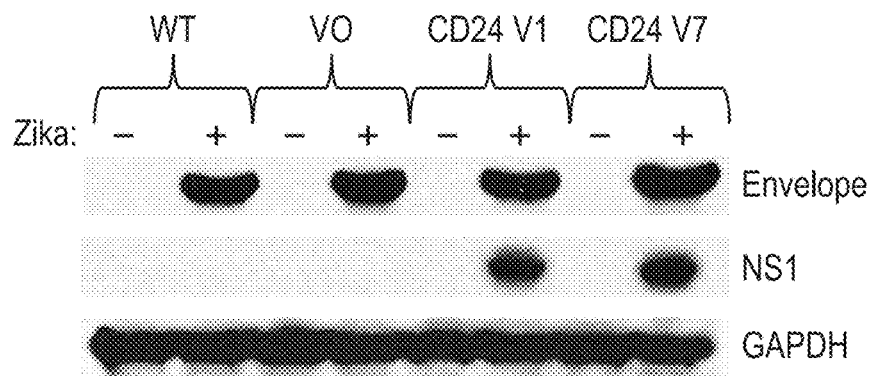
FIG. 8 depicts a Western blot of Zika virus NS1 and envelope proteins in SKNAS CD24 stable cells and Zika infection as compared to negative control siRNA and uninfected SKNAS CD24 cells.

Though the experiments indicate a relevance for CD24 in the productive Zika infection of neuroblastomas, the impact is difficult to judge in a transient system. To more accurately assess the impact of CD24 activity in this process, both splice variants (Variant 1 and variant 7) were stably expressed in SK-N-AS cells. Stable expression of the CD24 variants was then validated compared to "Vector Only" control cells and wild type SK-N-AS cells (FIG. 7). These two cell lines were then infected with Zika virus (MOI=10) and tested for their productivity (FIG. 8). The results indicated that, although all cells did indicate a robust presence of Zika Envelope protein, only the CD24 stable cells showed the presence of Zika NS1 protein, and thus Zika virus infection.

Figure 9B:
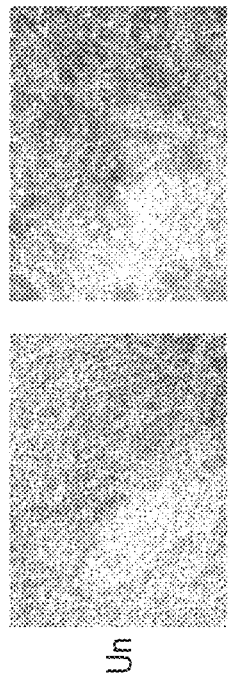
FIGS. 9A, 9B, 9C, and 9D depict bright field images of Zika virus infected CD24-expressing cells and control cells.
Figure 9B:
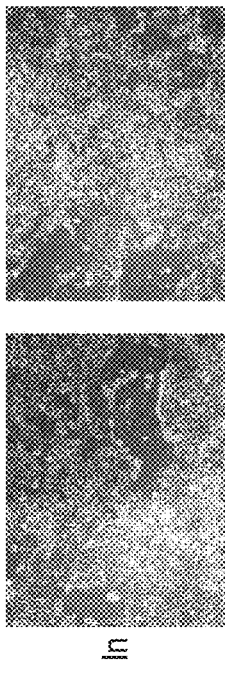
Figure 9D:
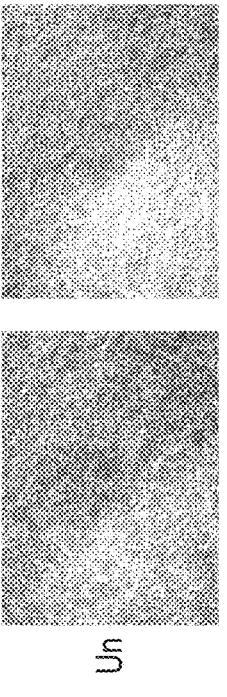
Figure 9D:
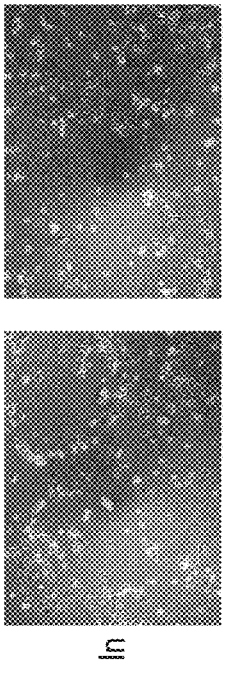
Figure 9A:
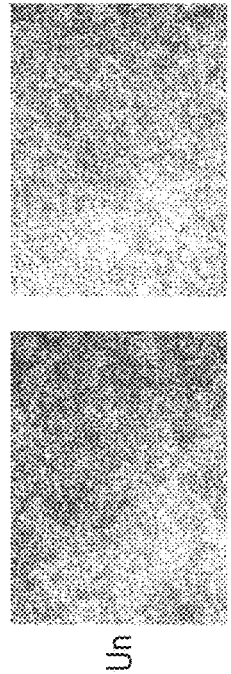
Figure 9A:
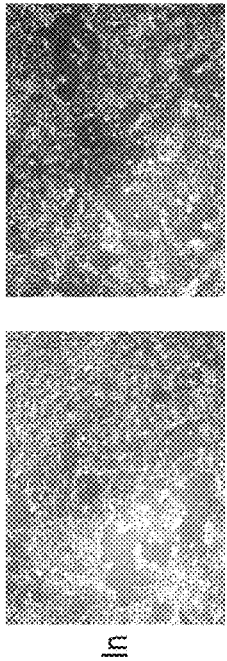
Figure 9C:
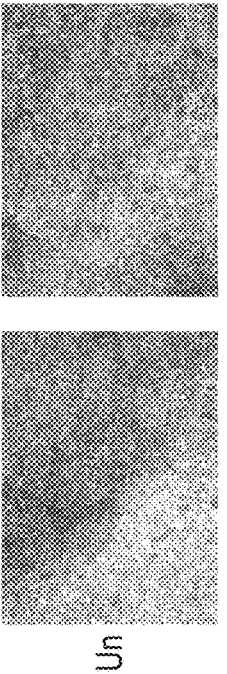
Figure 9C:

A bright field analysis of the cells revealed some loss of cells in the wild type (WT) and "Vector Only" (VO) cells (FIGS. 9A and 9B), but far more robust clearing in the CD24 variant 1-expressing cells (FIG. 9C), and a nearly total loss of cells in the CD24 variant 7-expressing cells (FIG. 9D). Comparing uninfected and Zika virus-infected cells, some loss can be observed in both WT and VO cells, correlating with the small initial loss of viability seen in FIG. 1. Yet, the majority of the cells remain intact. However, both CD24-expressing variant cell lines show dramatic cytopathic effects (CPE) and cell death by day 4. These data suggest that stable expression of both CD24 variants 1 and 7 can render SK-N-AS cells highly permissive to Zika virus infection.

Transgenic CD24 Expression in SK-N-AS Cells Increases Zika Virus Permissiveness

Figure 10A:
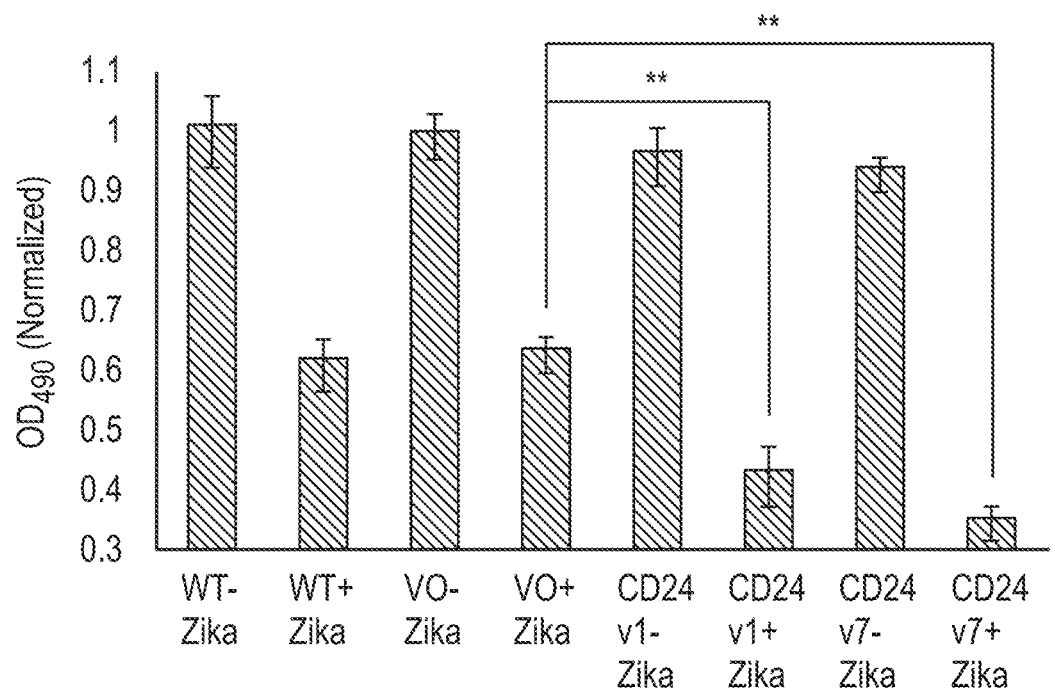
FIGS. 10A, 10B, 10C, 10D, and 10E depict CD24 expression renders SK-N-AS cells susceptible to Zika virus-induced cytotoxicity. Cell viability as determined by MTS assay (FIG. 10A) and apoptosis (caspase 3/7) assay (FIG. 10B) to examine the effect of Zika virus infection on SKNAS cells stably expressing CD24 (transcript variants 1 and 7 annotated as v1 and v7 respectively). Wild-type (WT) SK-N-AS cells, "Vector Only" (VO) SK-N-AS cells, and SK-N-AS cells expressing CD24 variant 1 (CD24 V1) and CD24 variant 7 (CD24 V7) were infected (MOI=10) for 96 hours, and then subjected to MTS and caspase 3/7 assays. Zika infected cells were compared to control cells treated with non-infected conditioned media. The results are representative of the combined data of experiments performed in sextuplicate (n=6), with error bars representing standard deviation.  p<0.05, Student's t-test.

The robust differences observed in Zika virus permissiveness, as shown in the bright field images in FIG. 9, suggest a dramatic change in the phenotype of CD24-expressing cells compared to their control cells after infection with Zika virus. To determine the cause of these changes, the cell samples were examined for changes in cell viability as performed in FIG. 1. The cell viability is shown in FIG. 10A.

Figure 10B:
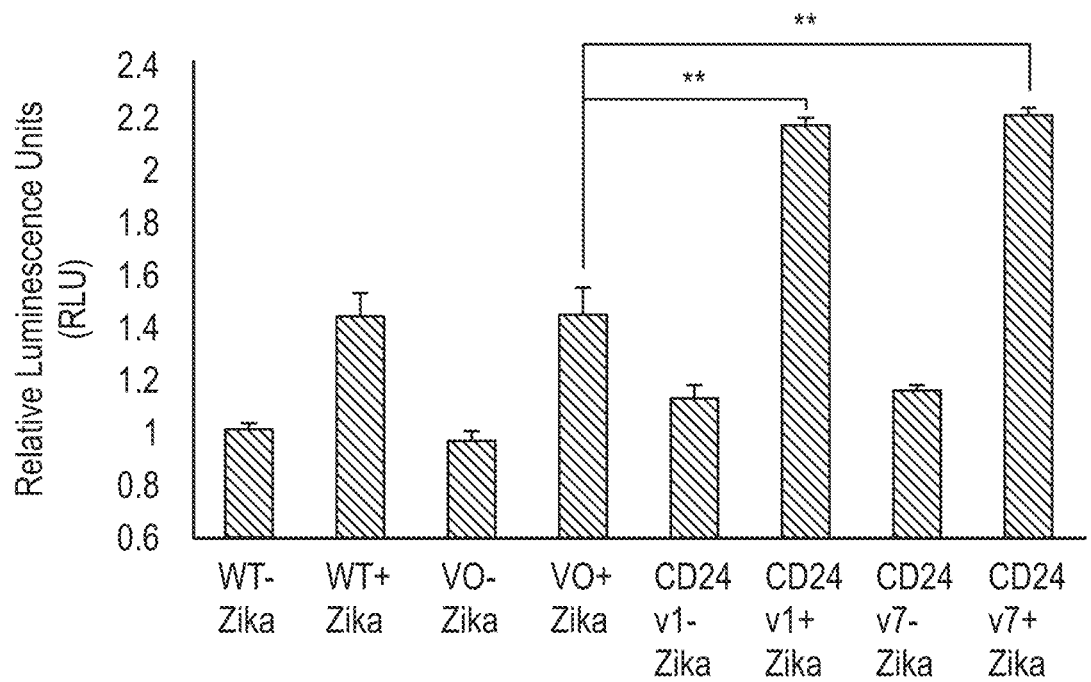

The results indicated that both WT and VO cells infected by Zika virus showed a marked decrease in viability, with losses varying between 30-35% of uninfected cells, consistent with FIG. 1. However, the presence of either CD24 variant dramatically decreased viability, ranging from a loss of 60-70% as compared to uninfected cells, indicating that cells were undergoing higher states of duress due to CPE. These data were further corroborated with a measurement of the rate of apoptosis (FIG. 10B). These results indicated that both WT and VO cells experienced a slight increase in their rates of apoptosis compared to uninfected cells, approximately 40% in both samples. In contrast, the CD24-expressing cell lines showed far more dramatic increases in apoptosis, more than double that observed in control cells (averaging ~ 220% of uninfected cells).

Figure 10C:
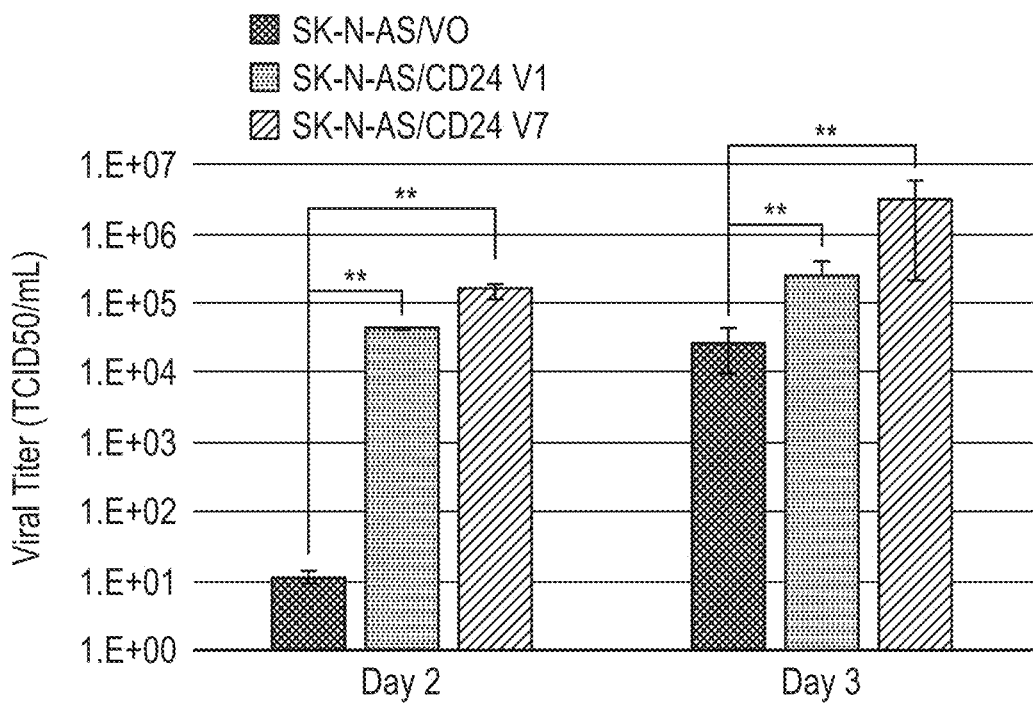
Figure 10D:
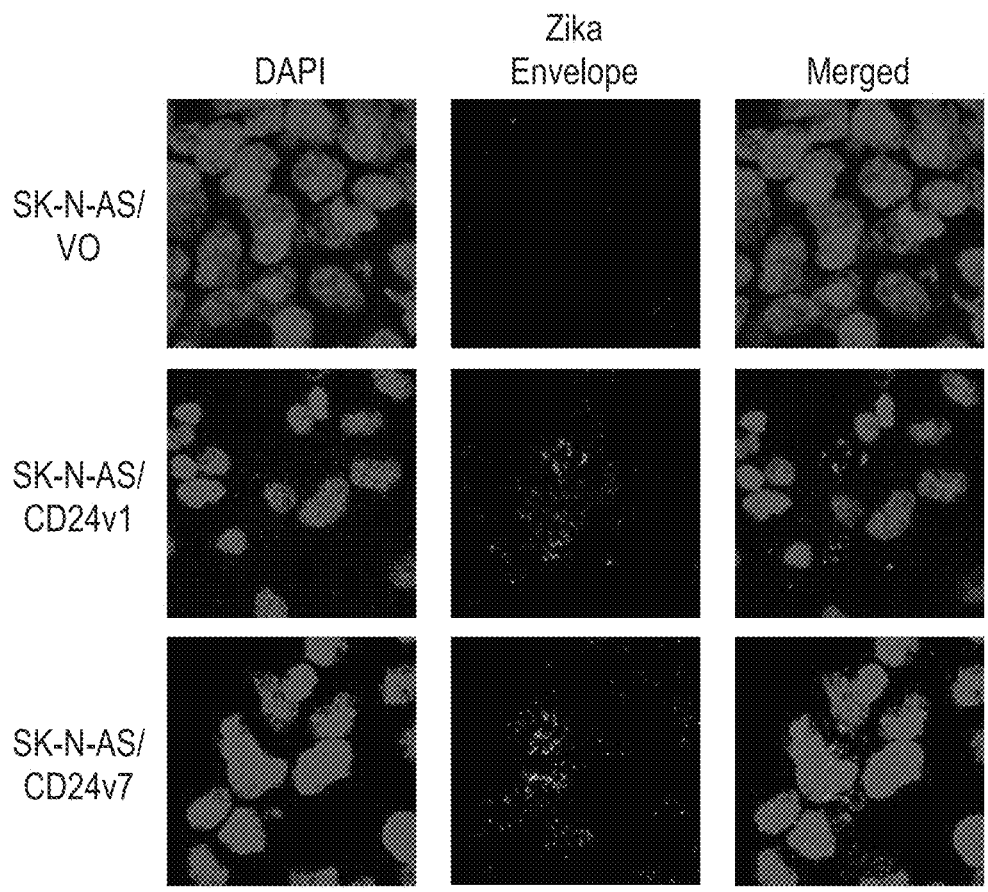
Figure 10E:
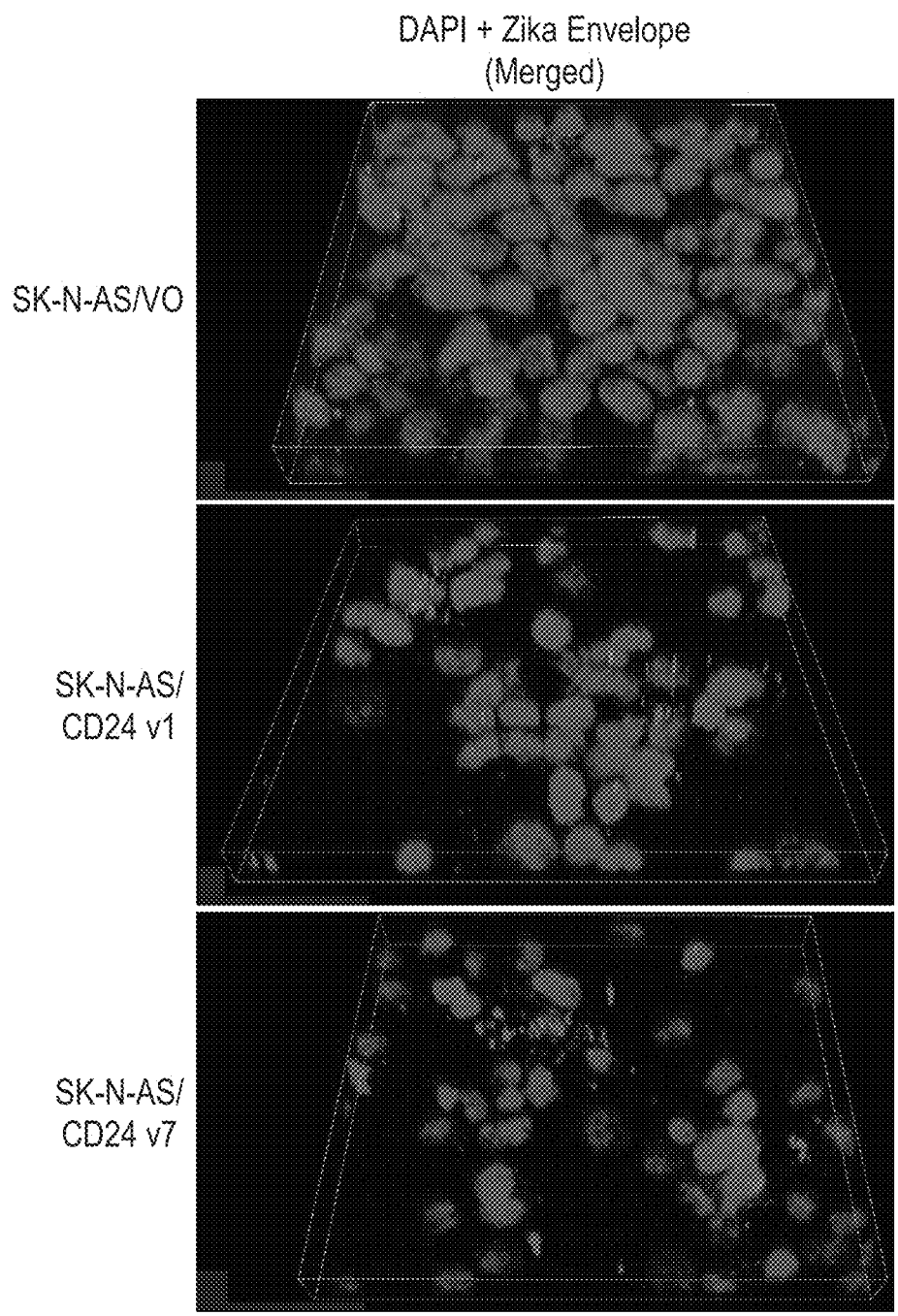
Figure 11:
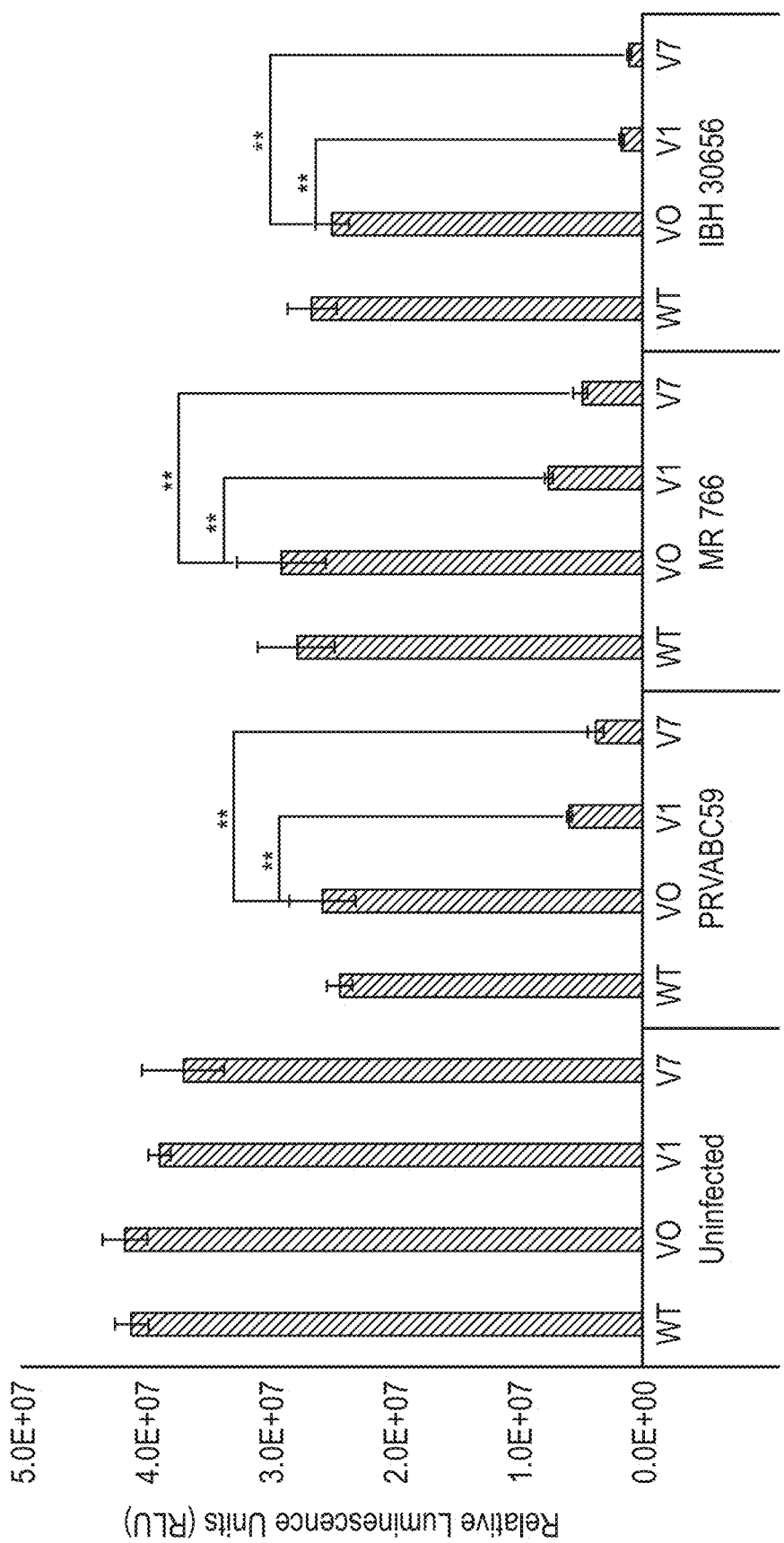
FIG. 11 depicts severe cytopathic effects induced by Zika virus strains PRVABC59, MR766 and IBH 30656 in CD24-expressing SK-N-AS cells. Wild-type (WT) SK-N-AS cells, Vector Only (VO) SK-N-AS cells, and SK-N-AS cells expressing CD24 variant 1 (CD24 v1) and CD24 variant 7 (CD24 v7) were infected with Zika virus reference strains PRVABC59, MR 766 and IBH 30656 (MOI=10). Zika infected cells were compared to control cells treated with non-infected conditioned media. After 96 hours, cellular ATP levels were measured and normalized to cell number. The results are representative of the combined data of experiments performed in triplicate, with error bars representing standard deviation. ** p<0.05, Student's t-test.
Figure 12:
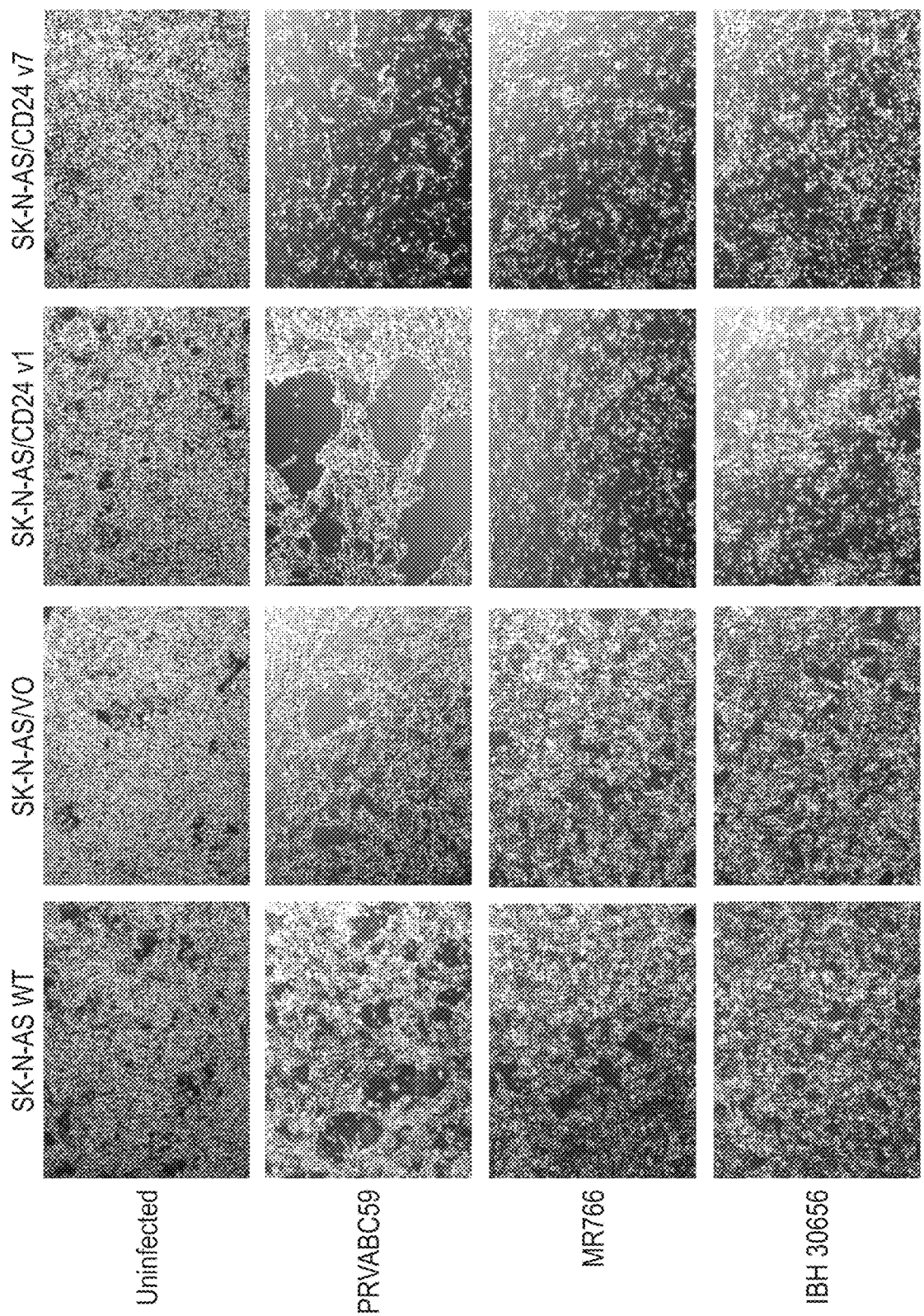
FIG. 12 depicts 3-dimensional Z-stacks of the immunofluorescent labeling of Zika viral Envelope protein in CD24-expressing SK-N-AS cells. Bright field images of control cells treated with non-infected conditioned media and Zika virus-infected SK-N-AS cells (96 hours after infection) comparing wild type (WT) cells to Vector Only (VO) cells, and to SK-N-AS cells stably expressing CD24 variant 1 (CD24 V1), and CD24 variant 7 (CD24 V7). Infections were performed in tandem for Zika strains PRVABC59, MR766 and IBH 30656 (MOI=10). Images were taken using a Nikon™ AIR VAAS laser point- and resonant-scanning confocal microscope (40×). All results are representative of the combined data of experiments performed in triplicate.
Figure 13A:
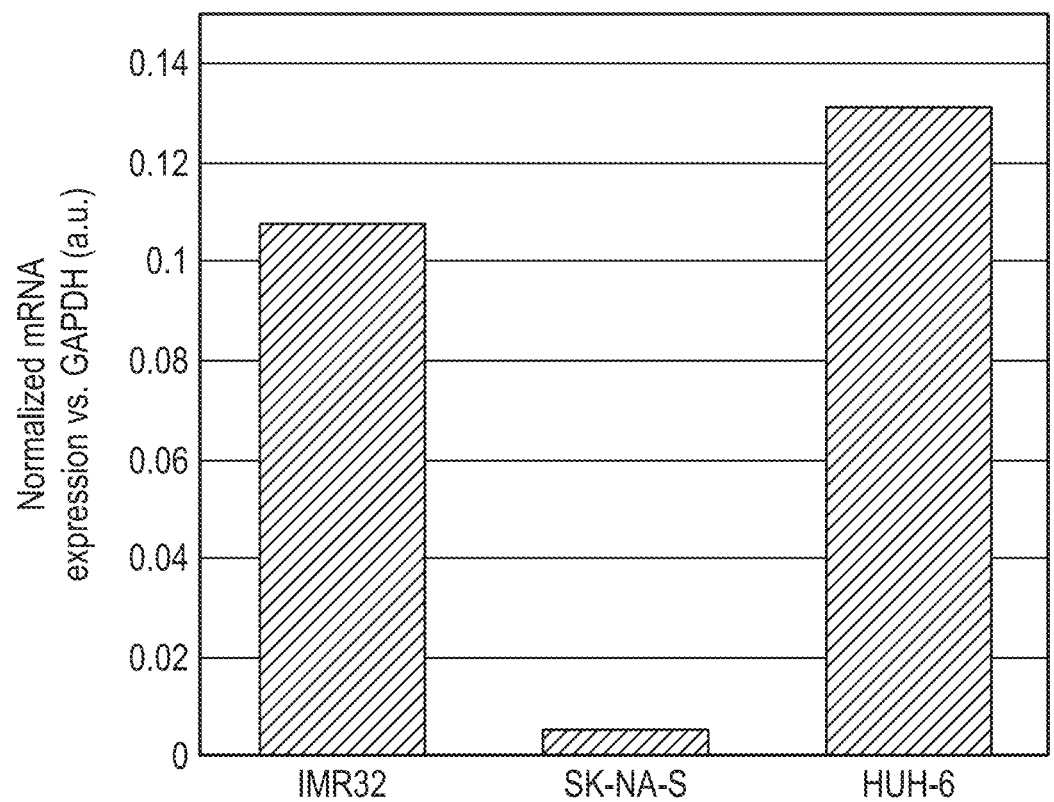
FIGS. 13A and 13B depict the observation that cells derived from hepatoblastoma are sensitive to Zika virus-mediated lysis.
Figure 13B:
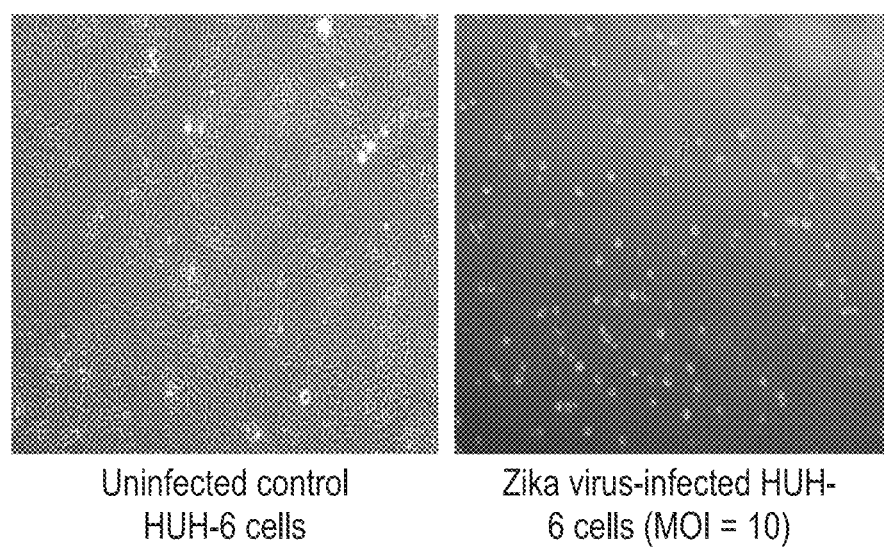
Figure 14:
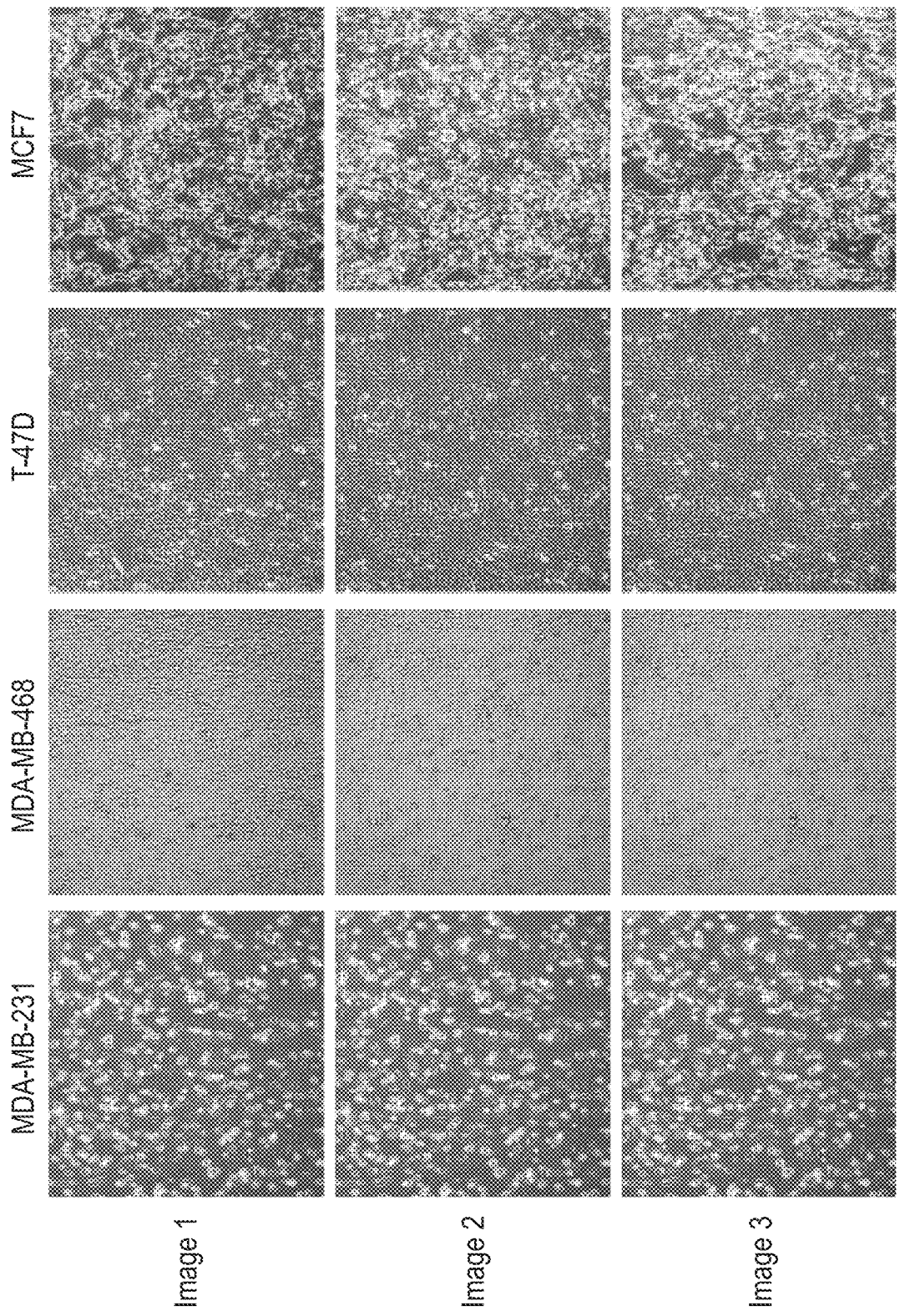
FIG. 14 depicts the observation that a breast cancer line is susceptible to Zika virus-mediated lysis. Cells were infected with Zika virus at MOI=10, and then incubated for 4 days. After 4 days, cells were photographed. Cell line MDA-BA231 was susceptible to Zika virus-induced lysis. Cell lines MDA-MB-468, T-470, and MCF7 were resistant.
Figure 15C:
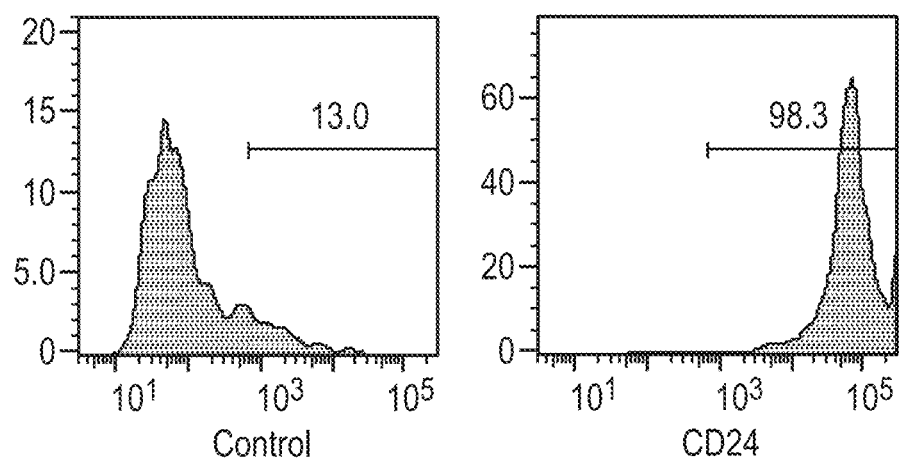

Viral titers within the culture media were also measured from these cells to determine if virus production coincided with cellular pathology (FIG. 10C). The results confirmed a startling increase in Zika virus production, with the presence of either CD24 variant 1 or 7 increasing viral titers by ~3-4 orders of magnitude compared to the VO controls at Day 2 post-infection (VO produced only $1\times10^1$ compared to $4\times10^4$ for variant 1 and $1\times10^5$ for variant 7). By Day 3 post-infection, viral titers remained ~10 to 100 fold greater in the CD24-expressing cells compared to controls ($2\times10^4$ versus $2\times10^5$ or $3\times10^6$, respectively).

Immunofluorescent labeling of Zika Envelope protein remained difficult to detect in SK-N-AS/VO cells, similar to that seen in wild type SK-N-AS cells. However, Zika Envelope protein was prominently expressed in both CD24-expressing stable cell line (FIG. 10D) and 3-dimensional Z-stacks again confirmed the presence of Envelope protein primarily in the cytoplasm of these cells (FIG. 10E).

Together, these data indicate that expression of either CD24 variant 1 or 7 renders SK-N-AS cells highly permissive to Zika virus cytotoxicity, and the mechanism of cell death includes induction of apoptosis. In addition, a correlation can be observed between viral pathology and an increase in viral titers produced in the presence of CD24 as well as the production of Zika Envelope protein in CD24-permissive cells.

Zika Virus Reference Strains MR766 and IBH 30656 Induce Severe Cytopathic Effects in CD24-Expressing SK-N-AS Cells To confirm that Zika virus-mediated cytotoxicity of CD24-expressing SK-N-AS cells was not limited to the PRVABC59 strain, the cytotoxicity of two additional Zika virus strains, MR 766 (ATCC® VR-1838; the Zika virus index strain, derived from a rhesus monkey in Uganda in 1947) and strain IBH 30656 (ATCC® VR-1839; a 1968 Nigerian human isolate), was also assessed. Zika virus strains PRVABC59, MR766, and IBH 30656 were assessed in parallel for their ability to induce cytopathic effects in CD24 variant 1- and 7-expressing SK-N-AS cells, as well as in wild type and Vector Only SK-N-AS control cells by infecting cells (MOI=10 for all respective strains) and examining them after 96 hours (FIG. 11). Similar to previous experiments, all Zika virus-infected cells exhibited some phenotypic effects after infection. In this case, viral toxicity was determined by comparing the amount of ATP depletion proportional to the number of host cells in culture. CD24-deficient wild-type (WT) and Vector-Only (VO) cells showed only mild decreases in cellular adenosine triphosphate (ATP) (equivalent to a loss of ~30-40% compared to uninfected cells), regardless of the strain of Zika virus screened. In contrast, in SK-N-AS cells that stably express CD24, Zika virus strains MR766 and IBH 30656 depleted ATP levels by 75-80% and 90-95%, respectively. Bright field images confirmed significant cytopathic effects and cell death in CD24-expressing cells, regardless of strain (FIG. 12). These results indicate that Zika virus cytopathic effects are far more dramatic in CD24-expressing cells and that this cytopathic effect can be induced even by divergent Zika virus strains.

It is important to note that therapy for neuroblastoma often includes the use of retinoids (13-cis-retinoic acid, isotretinoin) (see, e.g., Reynolds C P, Matthay K K, Villablanca J G, Maurer B J. Retinoid therapy of high-risk neuroblastoma. Cancer Lett. 2003 Jul. 18; 197 (1-2): 185-92). Retinoids are thought to drive differentiation of neuroblastoma cells to form benign ganglioneuroma. It is possible that retinoid treatment of neuroblastoma cells will lead to reduction or loss of CD24 expression, rendering the cells insensitive to Zika virus induced lysis. Thus, it may be important that patients with neuroblastoma who are to be treated with Zika viruses avoid retinoid therapy prior to Zika virus treatment.

Zika Viruses could be Useful for the Treatment of Other Tumors

As shown in FIG. 13A, HUH-6 hepatoblastoma cells express slightly higher levels of CD24 variant 1 mRNA than IMR32 cells. FIG. 13B show photographs of the Zika virus mediated lysis and a description of the experimental conditions used. These experimental data suggest that Zika viruses may be useful for the treatment of hepatoblastoma.

A triple-negative breast cancer line (MBA231) was identified to be susceptible to Zika virus-mediated lysis. FIG. 14 shows Zika virus-mediated lysis of the MBA231 cells. This experiment provides supportive data that Zika viruses may be useful for the treatment of breast cancer.

It is important to note that CD24 expression in breast cancer cells is suggested to be affected by previous breast cancer treatment. Specifically, previous treatment of breast cancer with taxanes is associated with increased expression of CD24 and decreased expression of CD44. Conversely, treatment of cancer cells with doxorubicin is associated with decreased expression of CD24 and increased expression of CD 44. It could be hypothesized that taxane-induced increases in CD24 expression may render cells previously resistant to Zika virus-induced lysis susceptible to Zika virus-induced lysis. Thus, it would be useful to study whether the taxane-induced increase in CD24 expression occurs with other tumors. For this, wild type SK-N-AS neuroblastoma cells (the neuroblastoma cell line that does not express CD24 and is resistant to Zika virus-mediated lysis) will be treated with paclitaxel to determine if paclitaxel treatment induces CD24 expression. It will be further determined whether paclitaxel or other taxanes increase CD24 expression in CD24-negative and CD24-heterogeneous tumors and cell lines.

Several brain tumors, including gliomas, glioblastomas, medulloblastomas, and pontine gliomas express CD24. Thus, Zika viruses could be used for treatment of CD24-positive malignant brain tumors. Similarly, benign brain tumors, neural sheath tumors, and tumors of the peripheral nervous system, including schwannomas and neurofibromatosis related tumors (including plexiform neurofibromatosis) likely express CD24. In addition, CD24 may be expressed on the tumors associated with tuberous sclerosis. Zika viruses and engineered Zika viruses may be used for treatment of CD24-positive benign central and peripheral nervous system tumors.

Three cell lines derived from HPV induced cervical tumors (HeLa cells, which maintain integrated HPV 18 genomes, and SiHa and CaSki cells, which maintain integrated HPV 16 genomes) were characterized for their susceptibility to Zika virus mediated lysis. For this, HeLa, SiHa, and CaSki cells were seeded at the concentration of $1 \times 10^5$ cells per well into a 12-well tissue culture treated plates and allowed to attach for 4-5 hrs under normal conditions for those cells. After attachment, the cells were infected with Zika virus at multiplicity of infection (moi) of 0.3 and maintained at 37° C., 5% $CO_2$. The media was replaced 16-18 hrs post infection. Cytopathic effect was observed in HeLa and CaSki cell lines within 72 hrs after infection, whereas in SiHa cell line cytopathic was observed within 7 days of infection. Thus, these three cell lines derived from HPV induced cervical tumors are susceptible to Zika virus-mediated lysis. The level of CD24 expression in the cells will be further characterized. Given the observed susceptibility, Zika viruses may be useful for the treatment of HPV associated pre-cancers and cancers, including cervical precancers and cancers, vaginal precancers and cancers, vulvar precancers and cancers, anal precancers and cancers, penile precancers and cancers, and HPV-positive oropharyngeal cancers.

Insofar as Zika viruses are thought to cause cell death by induction of autophagy with subsequent activation of cellular apoptosis (see, e.g., Chiramel A I et al., *Virus Res.* 2017 Sep. 9. pii: S0168-1702 (17) 30467-7. doi: 10.1016/j.virusres.2017. 09.006), Zika viruses may have a therapeutic role in the treatment of apoptosis-resistant tumors, restoring tumor cell sensitivity to proapoptotic agents by being given in combination with proapoptotic chemotherapy agents (e.g., anthracyclines).

Zika Viruses could be Useful for the Treatment of Diseases/Disorders Involved in CD24 Expression It was shown that resting T lymphocytes do not express significant levels of CD24. Nevertheless, activation of resting T cells with CD3/CD28 antibody leads to a marked increase in CD24 expression. These data indicate that CD3/CD28 antibody stimulation of CD4-positive T-cells (which are, at baseline, CD24-negative), markedly increased levels of CD24. Studies will now be performed to determine if CD24 expression confers to T-lymphocytes susceptibility to Zika virus-mediated lysis.

Because activation of T cells leads to increased CD24 expression, and because CD24 appears to be an important determinant of susceptibility to Zika virus mediated lysis, it can be proposed that other diseases associated with abnormal T cell activation might be amenable to therapeutic Zika virus-induced lysis of activated T cells.

As demonstrated in FIG. 15, unstimulated T cells derived from peripheral blood express little or no CD24. Stimulation of peripheral blood T cells with anti-CD3 and anti-CD28 antibodies leads to increasing expression of CD24 as measured on Day 3 and Day 10 after stimulation. Because these stimulated T cells express CD24, the CD24-expressing activated T-cells may be susceptible to Zika virus-mediated lysis. Targeted lysis of activated T cells could be used as a means of treating diseases associated with abnormal T cell activation or T cell mediated autoimmunity (i.e., autoimmune diseases that are not solely mediated through production of abnormal antibodies). Zika viruses may be used to target and destroy activated autoimmune T-cell clones, relieving symptoms and target order injury associated with abnormal T cell activation/T cell-mediated autoimmunity. There are many autoimmune diseases (e.g., list of diseases listed at the website of Autoimmune Registry, Inc. (ARI)) associated with abnormal T cell activation. Following are exemplary diseases that may be treated by an oncolytic Zika viruses: Rheumatologic disorders associated with abnormal T cell activation/T cell-mediated autoimmunity may include, but are not limited to, rheumatoid arthritis, juvenile idiopathic arthritis, systemic lupus erythematosus (including lupus nephritis and lupus vasculitis), pyomyositis, dermatomyositis, scleroderma, Sjogren's disease, ankylosing spondylitis, temporal arteritis, autoimmune vasculitis, sarcoidosis, Kawasaki disease, psoriatic arthritis, system sclerosis, Behçet's disease, and mixed connective tissue disorder.

Neurological diseases associated with abnormal T cell activation/T cell mediated autoimmunity may include, but are not limited to, multiple sclerosis, chronic inflammatory demyelinating polyneuropathy, and Guillain-Barré syndrome.

Gastroenterological diseases associated with abnormal T cell activation/T cell-mediated autoimmunity may include, but are not limited to, ulcerative colitis, Crohn's disease, primary biliary cirrhosis, autoimmune pancreatitis, and autoimmune hepatitis.

Dermatological diseases associated with abnormal T cell activation/T cell-mediated autoimmunity may include, but are not limited to, alopecia areata, psoriasis, vitiligo, and eczema.

Endocrine diseases associated with abnormal T cell activation/T cell-mediated autoimmunity may include, but are not limited to, Hashimoto thyroiditis, type 1 diabetes mellitus, Graves' disease, and autoimmune polyendocrine syndrome.

Hematological diseases associated with abnormal T cell activation/T cell-mediated autoimmunity may include, but are not limited to, autoimmune myelodysplastic syndromes, aplastic anemia, graft-versus-host disease, and hemophagocytic syndromes.

Infectious diseases associated with abnormal T cell activation/T cell-mediated autoimmunity may include, but are not limited to, HIV infection, post-transplantation lymphoproliferative disorder due to Epstein-Barr virus, and myocarditis.

Furthermore, while there are considerations to giving a potentially pathogenic virus to immune suppressed patients, insofar as Zika viruses may be used to target activated T-cell, Zika viruses could have a role in treatment of T-cell-mediated acute graft rejection.

Protocols for Experiments

The experiments for the discussion above were performed as follows.

Cell Lines Used & Conditions:

MR-32 cells were cultured in Minimum Essential Medium (MEM) Alpha and GlutaMAX™ [Gibco Life Sciences] supplemented with 10% fetal bovine serum [FBS]. SK-N-AS, 3T3, and Vero cells were cultured in Dulbecco's modified Eagle's medium (DMEM) [Gibco Life Sciences] supplemented with 10% FBS and 1% non-essential amino acids (NEAA). CHLA-42 cells were cultured in HyClone™ Iscove's Modified Dulbecco's Medium (IMDM) [GE Healthcare Life Sciences] supplemented with 20% FBS and 1×ITS (5 μg/mL insulin, 5 μg/mL transferrin, 5 ng/ml selenous acid). LA-N-6, SK-N-Be (1), and SMS-KAN cells were cultured in HyClone™ RPMI-1640 [GE Healthcare Life Sciences] supplemented with 10% FBS. 3T3 cells were acquired as a generous gift from the lab of Dr. Ken Alexander. All cells were incubated and maintained at 37° C. and 5% $CO_2$.

Cell Line Infection & Cell Viability Assays:

$10^4$ cells of each cell line were laid down in two rows in sextuplicate (thus, 12 wells total) in a flat bottom 96-well tissue culture treated plate and allowed to attach overnight. The following day, each cell line was either infected at an MOI=10 of Zika virus (strain=PR2015) or left uninfected (as controls). Six plates were prepared simultaneously for each cell line (allowing for assays on Days 0, 2, 4, 6, 8, & 10). All cells were maintained at 37° C. and 5% $CO_2$. Two hours after infection, the first plate was examined using the Cell-Titer 96® AQueous One Solution Cell Proliferation (MTS) assay (Promega Corp.) and used according to the manufacturer's instructions. All samples were read on a SpectraMax® M5 (Molecular Devices Corp.) system at a wavelength of 490 nm using SoftMax® Pro (version 6.2.1) software. Plates were examined again at each time point (Days 2, 4, 6, 8, & 10). Data graphed is the composite of experiments performed in triplicate.

Western Blot Analysis of Zika-Infected Cell Lines:

$2.5 \times 10^5$ cells were laid down in 12-well tissue culture treated plates and allowed to attach overnight. The following day, each cell line was either infected at an MOI=10 of Zika virus (strain=PR2015) or left uninfected (as controls). The plates were allowed to incubate for 4 days at 37° C. and 5% $CO_2$. Following the 4 day incubation, the cells were acquired and counted. $2 \times 10^5$ cells of each cell sample were boiled under denaturing conditions and proteins separated on 10% Tris-glycine denaturing polyacrylamide gels by electrophoresis. Proteins were transferred to nitrocellulose membranes and probed with the following primary antibodies: anti-NS1 (One World Lab, Cat #55964) at 1/200, anti-Env (Envelope) (GeneTex™, Cat #GTX133314) at 1/1000, and anti-GAPDH (Santa Cruz, FL-335) at 1/2000 according to standard methods. Blots were probed with horseradish peroxidase-conjugated secondary antibodies (Invitrogen™, Goat anti-Mouse, Cat #62-6520, Goat anti-Rb, Cat #65-6120) and visualized with ECL chemiluminescence (Pierce).

Quantitative Real-Time PCR

Total RNA was isolated from cells using an RNeasy Mini Kit (Qiagen™) and RNA concentrations were determined by UV spectrophotometry. Reverse transcription (RT) reactions were used to convert ~1.0 µg of total RNA into cDNA using the Applied Biosystems High Capacity cDNA RT kit (Thermo Fisher Scientific™). Reaction volumes were then brought to 100 µl with nuclease-free water. Quantitative real-time PCR (qPCR) was performed by using the CFX384 Touch Real-Time PCR Detection System (Bio-Rad Laboratories™, Hercules, CA). Gene-specific primers for quantitative real-time PCR were designed from their respective gene sequences using PrimerQuest® (Integrated DNA Technologies™) to generate sequences for PCR amplicons of 75 to 150 nucleotides that span exon-exon junctions. Gene-specific qPCR primer sequences used were as follows: GAPDH, sense primer, 5'-ACATCGCTCAGACACCATG-3' (SEQ ID NO: 1), and anti-sense primer, 5'-TGTAGTTGAGGTCAATGAAGGG-3' (SEQ ID NO: 2); CD24 variant 001, sense primer, 5'-CTGCTGCTGCTGGCACTGCTCC-3' (SEQ ID NO: 3), and anti-sense primer, 5'-GGGGCCAACCCAGAGTTGGAAG-3' (SEQ ID NO: 4); and CD24 variant 007, sense primer, 5'-CTGGGCCTGGGAGACCCTAGCG-3' (SEQ ID NO: 5), and anti-sense primer, 5'-GGGGCCAACCCAGAGTTGGAAG-3' (SEQ ID NO: 6). Synthetic double-stranded, linear DNA gBlock gene fragments (Integrated DNA Technologies™) corresponding to each gene-specific PCR amplicon were designed for qPCR standards. Standard curve copy numbers were calculated using the precise molecular weight of each dsDNA gBlock. The 384-well real-time PCR format included duplicate 10-fold dilutions of the linear dsDNA gene Block standards ranging from $2 \times 10^7$ to $2 \times 10^1$ copies per qPCR reaction. Human GAPDH was used to normalize the starting quantity of RNA. Reactions were performed in a 10-µl volume comprised of 2 µl of cDNA reaction, 5.0 ul of 2×SsoFast EvaGreen Supermix (Bio-Rad™), and 500 nM concentrations of each primer. The 2-step cycling parameters were 95° C. for 30 sec to activate the polymerase, followed by 40 cycles of 95° C. for 5 sec and 60° C. for 5 sec. Fluorescence measurements were taken at each cycle during the 60° C. annealing step. Melt curve analysis of generated PCR amplicons was performed upon completion of the 40 amplification cycles, which consisted of a 65° C. to 95° C. gradient at 0.5° C. increments for 2 sec plus fluorescence measurements. The copy number for each reaction was calculated by the CFX Manager 3.1 software (Bio-Rad™). Copy number values were normalized to the corresponding GAPDH values to determine the relative copy number.

Construction of CD24 Recombinant Expression Vectors:

Total RNA was isolated from IMR-32 cells using the RNeasy Mini Kit (Qiagen) and reverse transcribed using M-MLV reverse transcriptase. The cDNA was then used as a template for PCR amplification using GoTaq (Promega). The primers were designed as follows: CD24-001 ORF For (BamHI)-TGGATCCATGGGCAGAGCAATGGTGGCC (SEQ ID NO: 7), or CD24-007 ORF For (BamHI)-TGGATCCATGGTGGGACGATTCTGTCCC (SEQ ID NO: 8) and CD24 ORF Rev (EcoRI)-AGAATTCTTAAGAGTAGAGATGCAGAAGAGAGAGTG (SEQ ID NO: 9). Both PCR products were gel purified (QIAquick Gel Extraction kit, Qiagen), TOPO-cloned into pCR4-TOPO (Life Technologies), transformed into Top10 Chem comp cells and plated on LB Amp plates (100 µg/mL). Colonies were grown in LB Amp (100 µg/mL) overnight (O/N) at 37° C., with plasmids harvested by miniprep (QIAprep Spin Miniprep kit, Qiagen). All clones were sequenced (Retrogen™), then analyzed using VectorNTi and AlignX (Life Technologies). Both CD24 splice variants 001 and 007 were sub-cloned into pcDNA6/V5-HisA by restriction digestion using BamHI and EcoRI and ligated using T4 Ligase (NEB, Inc.). Final clones were confirmed by restriction digestion and quantified for transfection. The kits mentioned all were used pursuant to manufacturers' instructions.

Examination of Cells after Transient-Transfection of CD24 Cells Followed by Zika Infection:

SK-N-AS cells were seeded into single wells of a 6-well plate at a density of $2.5 \times 10^5$ cells per well and transfected using Fugene® 6 (Promega Corp.) with 2 µg of either pcDNA6/V5-HisA (Vector Only), pcDNA6/CD24-v001 or pcDNA6/CD24-v007. The transfection was allowed to continue 6 hours, after which the media was removed, the cells were washed with PBS, and fresh media was added. 48 hours after transfection, the cells were lifted (Accumax™), counted, and $2.8 \times 10^5$ cells of each sample were laid down in two wells of a 12-well tissue culture treated plate. Each sample was then either infected at an MOI=10 of Zika virus (strain=PR2015) or left uninfected (as controls). The samples were allowed to incubate for 4 additional days at 37° C. and 5% $CO_2$ after which they were acquired and counted. Western blot analysis was again performed (as above).

Western Blot Analysis of Native CD24 Expression in Neuroblastoma Cell Lines:

$2 \times 10^5$ cells of 6 neuroblastoma cell lines (i.e., IMR-32, SMS-KAN, SK-N-AS, LA-N-6, SK-N-Be (1), and CHLA-42 cells) along with Vero cells were acquired and counted, then boiled under denaturing conditions and proteins separated on an 12% Tris-Glycine denaturing polyacrylamide gels by electrophoresis. Proteins were transferred to nitrocellulose membranes (0.2 μm, BioRad™, Cat #1620112) and probed with the following primary antibodies: anti-CD24 (Monoclonal SN3, Cat #MA5-11828, ThermoFisher™) at 1/200, and anti-GAPDH (Santa Cruz, FL-335) at 1/2000 according to standard methods. Blots were probed with horseradish peroxidase-conjugated secondary antibodies (Invitrogen™, Goat anti-Mouse, Cat #62-6520) and visualized with ECL chemiluminescence (Pierce™).

Examination of IMR-32 Cells after Transient-Transfection of CD24 siRNA into Cells Followed by Zika Infection:

IMR-32 cells were seeded into single wells of a 6-well plate at a density of $2.5 \times 10^5$ cells per well and transfected with 50 μM of CD24 Silencer Select Pre-designed siRNA (Cat #4392420, ID: s2616) or Silencer Select Negative Control siRNA #1 (Cat #4390843). The transfection was allowed to continue 6 hours, after which the media was removed, the cells were washed with 1× phosphate buffered saline (PBS), and fresh media was added. 48 hours after transfection, the cells were lifted (Accumax™), counted, and $2.8 \times 10^5$ cells of each sample were laid down in two wells of a 12-well tissue culture treated plate. Each sample was then either infected at an MOI=10 of Zika virus (strain=PR2015) or left uninfected (as controls). The samples were allowed to incubate for 4 additional days at 37° C. and 5% $CO_2$ after which they were acquired and counted. Western blot analysis was performed once again (as above).

Construction of SK-N-AS Cells Stably-Expressing CD24 Variants 1 and 7:

SK-N-AS cells were seeded into single wells of a 6-well plate at a density of $2.5 \times 10^5$ cells per well and transfected using Fugene® 6 (Promega Corp.) with 2 μg of either pcDNA6/V5-HisA (Vector Only), pcDNA6/CD24-v001, or pcDNA6/CD24-v007. The transfection was allowed to continue 6 hours, after which the media was removed, the cells were washed with PBS, and fresh media was added. 24 hours after transfection, the cells began selection at 6 μg/mL with Blasticidin (Life Technologies Corp.). Selection continued for 10 days until individual colonies could be isolated.

Validation of SK-N-AS Cells Stably-Expressing CD24 Variants 1 and 7:

$2.5 \times 10^5$ cells of each selected SK-N-AS cell sample (to include WT SK-N-AS, SK-N-AS/VO, SK-N-AS/CD24-v001, and SK-N-AS/CD24-v007) were acquired and counted, then boiled under denaturing conditions and proteins separated on an 18% Tris-Glycine denaturing polyacrylamide gel by electrophoresis. Proteins were transferred to nitrocellulose membranes and probed with the following primary antibodies: anti-CD24 (Monoclonal SN3, Cat #MA5-11828, ThermoFisher) at 1/200, and anti-GAPDH (Santa Cruz, FL-335) at 1/2000 according to standard methods. Blots were probed with horseradish peroxidase-conjugated secondary antibodies and visualized with ECL chemiluminescence (Pierce).

Examination of SK-N-AS CD24 Stable Cells Following Zika Infection:

$2.8 \times 10^5$ cells of each selected SK-N-AS cell sample (to include WT SK-N-AS, SK-N-AS/VO, SK-N-AS/CD24-v001, and SK-N-AS/CD24-v007) were laid down in two wells of a 12-well tissue culture treated plate. Each sample was then either infected at an MOI=10 of Zika virus (strain=PR2015) or left uninfected (as controls). The samples were allowed to incubate for 4 additional days at 37° C. and 5% $CO_2$. The plates were then examined under bright field conditions using a Nikon™ AIR VAAS laser point-and resonant-scanning confocal microscope, after which they were acquired and counted for examination by Western blot analysis (as above).

Cell Viability (MTS) of SK-N-AS CD24 Stable Cells Following Zika Infection:

$8 \times 10^3$ cells were seeded into 12 wells of a 96-well plate for each SK-N-AS sample (to include WT SK-N-AS, SK-N-AS/VO, SK-N-AS/CD24-v001, and SK-N-AS/CD24-v007). Each sample was then either infected at an MOI=10 of Zika virus (strain=PR2015) or left uninfected (as controls) (thus, each sample was performed in sextuplicate). The samples were allowed to incubate for 4 additional days at 37° C. and 5% $CO_2$. After treatment, the CellTiter 96® Aqueous One Solution Cell Proliferation (Promega Corp.) assay was performed according to the manufacturer's instructions (PerkinElmer™ Multilabel Plate Reader-Model 2104) with each well measured in triplicate.

Caspase 3/7 Assay of SK-N-AS CD24 Stable Cells Following Zika Infection:

$8 \times 10^3$ cells were seeded into 12 wells of a 96-well plate for each SK-N-AS sample (to include WT SK-N-AS, SK-N-AS/VO, SK-N-AS/CD24-v001, and SK-N-AS/CD24-v007). Each sample was then either infected at an MOI=10 of Zika virus (strain=PR2015) or left uninfected (as controls) (thus, each sample was performed in sextuplicate). The samples were allowed to incubate for 4 additional days at 37° C. and 5% $CO_2$. After treatment, Caspase-Glo® 3/7 (Promega Corp.) reagent was added to each well, and allowed to incubate at room temperature for 2 hrs. Caspase activity was then measured for luminescence using a GloMax® luminometer (Promega) with each well measured in triplicate.

Construction of 3T3 and Vero Cells Stably-Expressing CD24 Variants 1 and 7:

3T3 or Vero cells will be seeded into single wells of a 6-well plate at a density of $2.5 \times 10^5$ cells per well and transfected using Fugene® 6 (Promega Corp.) with 2 μg of either pcDNA6/V5-HisA (Vector Only), pcDNA6/CD24-v001 or pcDNA6/CD24-v007. The transfection will continue for 6 hours, after which the media will be removed, the cells washed with 1×PBS, and fresh media will be added. 24 hours after transfection, the cells will begin selection with Blasticidin (Life Technologies Corp.) as described in the experiments above. Selection will continue until individual colonies can be isolated and assayed.

The disclosures of each and every patent, patent application, GenBank record, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope used in the practice of the invention. The appended claims are intended to be construed to include all such embodiments and equivalent variations.

We claim:

1. A pharmaceutical composition comprising:
   (a) a naked viral RNA of an oncolytic Zika virus in a liposome or a micelle and a pharmaceutically acceptable carrier, or
   (b) a pharmaceutically acceptable carrier and a unit dosage form of an oncolytic Zika virus,
   wherein the naked RNA of the oncolytic Zika virus or the oncolytic Zika virus is in an amount sufficient to reduce the size of a CD24 positive tumor upon administration to a subject in need of treatment for a CD24 positive tumor, and wherein the oncolytic Zika virus is selected from the group consisting of: PRVABC59, MR766 and IBH30656.

2. The pharmaceutical composition of claim 1, wherein the unit dosage form of the oncolytic Zika virus comprises about $10^2$ pfu to about $10^{13}$ pfu of the oncolytic Zika virus.

3. The pharmaceutical composition of claim 1, wherein the pharmaceutical composition is formulated for intratumoral administration, intradermal administration, subcutaneous administration, or intravenous administration.

4. A combination therapy comprising a pharmaceutical composition of
(a) a naked viral RNA of an oncolytic Zika virus in a liposome or a micelle and a pharmaceutically acceptable carrier, or
(b) a pharmaceutically acceptable carrier and a unit dosage form of an oncolytic Zika virus
and an immunosuppressive therapy that enhances cell lysis induced by administration of the naked viral RNA of an oncolytic Zika virus or the oncolytic Zika virus, and wherein the oncolytic Zika virus is selected from the group consisting of: PRVABC59, MR766 and IBH30656.

5. The combination therapy of claim 4, wherein the immunosuppressive therapy comprises:
a) administration of an immunosuppressive pharmaceutical agent,
b) administration of an antivirus antibody, the antivirus antibody capable of recognizing the oncolytic Zika virus; or
c) plasmapheresis to remove the antivirus antibody.

6. The combination therapy of claim 5, wherein the combination therapy is for treating an individual having a CD24 positive tumor and further comprises administering an anti-neoplasm treatment selected from the group consisting of: a chemotherapy, a radiotherapy, surgery, a hormone therapy, an immunotherapy, and a combination thereof.

7. A method for treating a CD24 positive disease in an individual in need of such treatment comprising:
administering a therapeutically effective amount of the pharmaceutical composition of claim 1, wherein the disease is a CD26 positive tumor.

8. A method for treating a CD24 positive disease in an individual in need of such treatment comprising administering a therapeutically effective amount of the combination therapy of claim 4, wherein the disease is a CD24 positive tumor.

9. The method of claim 7, wherein the CD24 positive disease is a CD24 positive tumor selected from the group of: an ovarian cancer, a colorectal cancer, a B cell lymphoma, erythroleukemia, a glioma, a small cell lung cancer, an esophageal squamous cell carcinoma, a hepatocellular carcinoma, a hepatoblastoma, a cholangiocarcinoma, a pancreatic adenocarcinoma, a melanoma, an urothelial carcinoma, a breast cancer, a primary neuroendocrine carcinoma, a neural sheath tumor, a peripheral nervous system tumor, a neurofibroma, a schwannoma, a neural crest-derived tumor, an HPV-associated malignancy, an Epstein-Barr virus-induced malignancy, and a prostate carcinoma.

10. The method of claim 8, wherein the CD24 positive tumor is selected from the group of: an ovarian cancer, a colorectal cancer, a B cell lymphoma, erythroleukemia, a glioma, a small cell lung cancer, an esophageal squamous cell carcinoma, a hepatocellular carcinoma, a hepatoblastoma, a cholangiocarcinoma, a pancreatic adenocarcinoma, a melanoma, an urothelial carcinoma, a breast cancer, a primary neuroendocrine carcinoma, a neural sheath tumor, a peripheral nervous system tumor, a neurofibroma, a schwannoma, a neural crest-derived tumor, an HPV-associated malignancy, an Epstein-Barr virus-induced malignancy, and a prostate carcinoma.

11. The method of claim 9, wherein the CD24 positive tumor is a resistant or a refractory tumor.

12. The method of claim 10, wherein the CD24 positive tumor is a resistant or a refractory tumor.

13. The method according to claim 9, wherein the HPV-associated malignancy is selected from the group consisting of: a cervical cancer or precancer; a penile, vaginal, vulvar, and anal precancer or cancer; and an oropharyngeal precancer or cancer.

14. The method according to claim 10, wherein the HPV-associated malignancy is selected from the group consisting of: a cervical cancer or precancer; a penile, vaginal, vulvar, and anal precancer or cancer; and an oropharyngeal precancer or cancer.

15. The method of claim 9, wherein the CD24 positive disease is an Epstein-Barr virus-induced malignancy selected from the group consisting of: a nasopharyngeal carcinoma, a lymphoma, and a post transplantation lymphoma proliferative disease.

16. The method of claim 10, wherein the CD24 positive disease is an Epstein-Barr virus-induced malignancy selected from the group consisting of: a nasopharyngeal carcinoma, a lymphoma, and a post transplantation lymphoma proliferative disease.

* * * * *